US012097371B2

(12) United States Patent
Brown et al.

(10) Patent No.: US 12,097,371 B2
(45) Date of Patent: Sep. 24, 2024

(54) AURICULAR NERVE FIELD STIMULATION DEVICE

(71) Applicant: Neuraxis, Inc., Versailles, IN (US)

(72) Inventors: Christopher R. Brown, Greensburg, IN (US); Gary M. Peterson, Versailles, IN (US)

(73) Assignee: Neuraxis, Inc., Versailles, IN (US)

( * ) Notice: Subject to any disclaimer, the term of this patent is extended or adjusted under 35 U.S.C. 154(b) by 254 days.

(21) Appl. No.: 17/715,121

(22) Filed: Apr. 7, 2022

(65) Prior Publication Data

US 2022/0226654 A1   Jul. 21, 2022

Related U.S. Application Data

(62) Division of application No. 17/040,766, filed as application No. PCT/US2019/029172 on Apr. 25, 2019, now Pat. No. 11,369,791.

(Continued)

(51) Int. Cl.
*A61N 1/36* (2006.01)
*A61N 1/04* (2006.01)
*A61N 1/05* (2006.01)

(52) U.S. Cl.
CPC ....... *A61N 1/36038* (2017.08); *A61N 1/0456* (2013.01); *A61N 1/0541* (2013.01);
(Continued)

(58) Field of Classification Search
CPC ...................................... A61N 1/36036–36039
See application file for complete search history.

(56) References Cited

U.S. PATENT DOCUMENTS

| 4,646,744 A | 3/1987 | Capel |
| 4,865,048 A | 9/1989 | Eckerson |

(Continued)

FOREIGN PATENT DOCUMENTS

| AT | 395106 B | 9/1992 |
| EP | 2474339 A1 | 11/2012 |

(Continued)

OTHER PUBLICATIONS

Office action for copending Korean Patent Application No. 10-2020-7034010, dated Jan. 22, 2024. Translation appended.

(Continued)

*Primary Examiner* — Eric D. Bertram
(74) *Attorney, Agent, or Firm* — Barnes & Thornburg LLP

(57) ABSTRACT

An auricular nerve field stimulation device may include first non-percutaneous electrodes arranged to contact a ventral aspect of an auricle, second non-percutaneous electrodes arranged to contact a dorsal aspect of the auricle, and electrical circuitry coupled to the electrodes and configured to selectively apply electrical stimulation signals to the electrodes to cause a first set of trans-auricular currents to flow through the auricle between the first electrodes and respective ones of the second electrodes paired therewith according to a first pairing, and to cause a second set of trans-auricular currents to flow through the auricle between the first electrodes and respective ones of the second electrodes paired therewith according to a second pairing different from the first pairing, the first and second sets of trans-auricular currents to stimulate at least one auricular nerve field within the auricle.

19 Claims, 10 Drawing Sheets

Related U.S. Application Data

(60) Provisional application No. 62/662,995, filed on Apr. 26, 2018.

(52) U.S. Cl.
CPC ..... *A61N 1/36017* (2013.01); *A61N 1/36021* (2013.01); *A61N 1/36036* (2017.08)

(56) References Cited

U.S. PATENT DOCUMENTS

| | | | |
|---|---|---|---|
| 5,084,007 | A | 1/1992 | Malin |
| 5,094,242 | A * | 3/1992 | Gleason ............ A61N 1/36071 606/189 |
| 5,458,625 | A | 10/1995 | Kendall |
| 6,212,433 | B1 | 4/2001 | Behl |
| 6,296,652 | B1 | 10/2001 | Qingman |
| 7,092,849 | B2 | 8/2006 | Lafitte et al. |
| 7,103,417 | B1 * | 9/2006 | Segel ................ A61N 1/36038 607/57 |
| 8,428,719 | B2 | 4/2013 | Napadow |
| 8,761,872 | B2 * | 6/2014 | Hinrichsen ......... A61H 39/002 607/2 |
| 8,942,814 | B2 * | 1/2015 | Szeles ............... A61H 39/002 607/45 |
| 9,662,269 | B2 * | 5/2017 | Brown ............... A61N 1/36017 |
| 9,782,584 | B2 * | 10/2017 | Cartledge ............ A61N 1/0472 |
| 9,839,577 | B2 | 12/2017 | Brown |
| 9,901,734 | B2 * | 2/2018 | Bennett ............. A61N 1/36017 |
| 10,010,479 | B2 | 3/2018 | Brown |
| 10,052,257 | B2 * | 8/2018 | Nageshwar ......... A61H 39/002 |
| 10,058,478 | B2 | 8/2018 | Schnetz et al. |
| 10,086,199 | B2 | 10/2018 | Brown |
| 10,130,275 | B2 | 11/2018 | Nageshwar |
| 10,413,119 | B2 | 9/2019 | Robertson |
| 10,695,568 | B1 * | 6/2020 | Covalin ............. A61H 39/002 |
| 10,806,928 | B2 * | 10/2020 | Sharma ............ A61N 1/36036 |
| 11,369,791 | B2 * | 6/2022 | Brown ............... A61N 1/0476 |
| 2003/0050470 | A1 | 3/2003 | An et al. |
| 2003/0149451 | A1 | 8/2003 | Chomenky et al. |
| 2004/0044390 | A1 * | 3/2004 | Szeles ...................... A61N 1/32 607/142 |
| 2006/0122675 | A1 * | 6/2006 | Libbus ................ A61N 1/0551 607/116 |
| 2008/0051852 | A1 * | 2/2008 | Dietrich .............. A61H 39/002 607/45 |
| 2008/0146549 | A1 | 6/2008 | Coleman |
| 2008/0249439 | A1 | 10/2008 | Tracey et al. |
| 2010/0004715 | A1 | 1/2010 | Fahey |
| 2010/0113965 | A1 | 5/2010 | Kanevsky et al. |
| 2010/0168822 | A1 | 7/2010 | Szales |
| 2010/0262205 | A1 | 10/2010 | DeRidder |
| 2011/0160811 | A1 * | 6/2011 | Walker ................. A61N 1/0452 607/2 |
| 2011/0190569 | A1 | 8/2011 | Simon |
| 2012/0035680 | A1 | 2/2012 | Napadow |
| 2012/0226333 | A1 * | 9/2012 | Szeles .................. A61H 39/002 607/59 |
| 2013/0150923 | A1 * | 6/2013 | Schnetz ............ A61N 1/36034 607/59 |
| 2014/0081368 | A1 | 3/2014 | Szales |
| 2014/0370476 | A1 | 12/2014 | Nageshwar |
| 2014/0371608 | A1 | 12/2014 | Nageshwar |
| 2014/0371621 | A1 | 12/2014 | Nageshwar |
| 2015/0112405 | A1 * | 4/2015 | Brown .................. A61H 39/02 607/46 |
| 2015/0265830 | A1 | 9/2015 | Simon |
| 2015/0360030 | A1 * | 12/2015 | Cartledge ............ A61N 1/3603 607/136 |
| 2016/0113526 | A1 | 4/2016 | Nageshwar |
| 2017/0087364 | A1 * | 3/2017 | Cartledge ................ A61N 1/18 |
| 2017/0143247 | A1 | 5/2017 | Nageshwar |
| 2017/0197081 | A1 | 7/2017 | Charlesworth et al. |
| 2018/0064603 | A1 | 3/2018 | Brown |
| 2018/0200522 | A1 * | 7/2018 | Taca, Jr. ............. A61N 1/36089 |
| 2018/0296435 | A1 | 10/2018 | Brown |
| 2019/0262229 | A1 | 8/2019 | Brown |
| 2022/0072311 | A1 | 3/2022 | Taca, Jr. |

FOREIGN PATENT DOCUMENTS

| | | |
|---|---|---|
| WO | 2005001706 A1 | 1/2005 |
| WO | 2011030210 A1 | 3/2011 |
| WO | 2014200488 A1 | 12/2014 |
| WO | 2014200489 A2 | 12/2014 |
| WO | 2014200492 A1 | 12/2014 |
| WO | 2014207512 A1 | 12/2014 |
| WO | 2017/044967 A1 | 3/2017 |

OTHER PUBLICATIONS

Miranda, Adrian, and Arturo Taca. "Neuromodulation with percutaneous electrical nerve field stimulation is associated with reduction in signs and symptoms of opioid withdrawal: a multisite, retrospective assessment." The American journal of drug and alcohol abuse vol. 44,1 (2018): 56-63. doi:10.1080/00952990.2017.1295459.

Roberts, Arthur and Christopher R. Brown. "Percutaneous Peri-Auricular Peripheral Nerve Field Stimulation: A Novel, Non-Opioid Therapy for Diabetic Neuropathy." The Pain Practitioner, vol. 25, 3 (2015): 41-47.

First Office Action issued in co-pending Japanese Application No. 2021-50996, dated of Dec. 22, 2022.

PCT International Search Report and Written Opinion completed by the ISA/US on Jan. 2, 2020 and issued in connection with PCT/US2019/029172.

Non-Final Office Action dated Mar. 19, 2018 filed in U.S. Pat. No. 10,010,479 issued Jul. 3, 2018.

Response and Terminal Disclaimer filed Apr. 10, 2018 to Non-Final Action dated Mar. 19, 2018 in U.S. Pat. No. 10,010,479 issued Jul. 3, 2018.

Non-Final Office Action dated Aug. 2, 2017 filed in U.S. Pat. No. 9,839,577 issued Dec. 12, 2017.

Response and Terminal Disclaimer filed Sep. 7, 2017 to Non-Final Office Action dated Aug. 2, 2017 in U.S. Pat. No. 9,839,577 issued Dec. 12, 2017.

Non-Final Office Action Dated Jul. 15, 2015 filed in U.S. Pat. No. 9,662,269 issued May 30, 2017.

Response filed Nov. 16, 2015 to Non-Final Office Action dated Jul. 15, 2015 in U.S. Pat. No. 9,662,269 Issued May 30, 2017.

Final Office Action dated Feb. 25, 2016 filed in U.S. Pat. No. 9,662,269 issued May 30, 2017.

Response and Request for Continued Examination filed on Jun. 27, 2016 to Final Office Action dated Feb. 25, 2016 in U.S. Pat. No. 9,662,269 issued May 30, 2017.

Non-Final Office Action dated Jul. 28, 2016 filed in U.S. Pat. No. 9,662,269 issued May 30, 2017.

Response filed Aug. 25, 2016 to Non-Final Office Action dated Jul. 28, 2016 filed in U.S. Pat. No. 9,662,269 Issued May 30, 2017.

Extended European Search Report in Application No. 19850021.7-1122 dated Dec. 17, 2021.

* cited by examiner

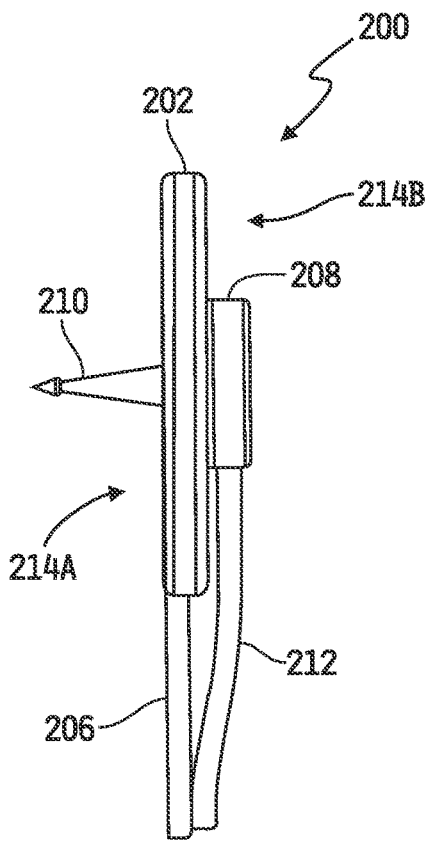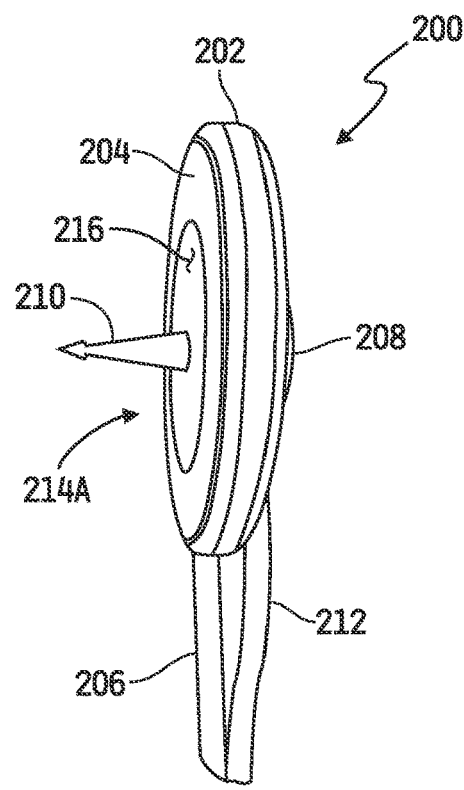
FIG. 9A  FIG. 9B
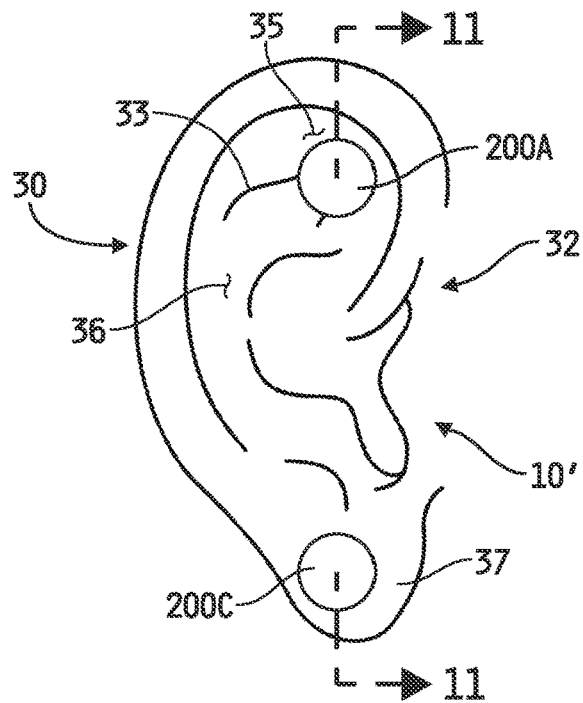
FIG. 10

AURICULAR NERVE FIELD STIMULATION DEVICE

CROSS-REFERENCE TO RELATED APPLICATION

This is a divisional application of U.S. patent application Ser. No. 17/040,766, filed Sep. 23, 2020 and issued as U.S. Pat. No. 11,369,791, which is a U.S. national stage entry of PCT Application No. PCT/US2019/029172, filed Apr. 25, 2019, which claims the benefit of and priority to U.S. Provisional Patent Application Ser. No. 62/662,995, filed Apr. 26, 2018, the disclosures of which are incorporated herein by reference in their entireties.

FIELD OF THE DISCLOSURE

This disclosure relates generally to electrical stimulation devices, and more specifically to auricular stimulation devices for stimulating auricular nerve fields.

BACKGROUND

Percutaneous electrical stimulation devices are known and used to provide therapy to humans and animals. As one example of such devices, conventional electrical acupuncture devices are used to percutaneously supply electrical stimulation to acupuncture points including those in the region of the ear.

Located within the ear are cranial nerves V, VII, IX, X which anastomose (connect) directly into the brain and branches of the greater and lesser occipital nerves anastomosing directly into the cervical spine. There are distinct areas of the auricle on both the dorsal and ventral aspect which carry a predominance/concentration of the cranial nerves, peripheral nerves, arterial branches, and neurovascular bundles. In this regard, other known electrical stimulation devices are used to percutaneously supply electrical stimulation to such auricular peripheral nerve fields for various purposes including pain management.

Non-percutaneous electrical stimulation devices are also known and used to provide therapy to humans and animals. One example of such a non-percutaneous device is a conventional transcutaneous electrical nerve stimulation (TENS) device which typically uses two or more non-percutaneous electrodes spaced apart along an area or region of the skin of a human or animal to provide low-voltage current to the surface of the skin for the purpose of pain management. One particular class of TENS devices includes so-called interferential therapy (IFT) or interferential current (IFC) devices which typically use four or more non-percutaneous electrodes spaced apart along an area or region of the skin. The operation of conventional IFT devices differ from conventional TENS in that voltages with differing frequencies are applied across diagonally-spaced pairs of the electrodes to create lower frequency "interference" currents in a region of the anatomy located between the four spaced-apart electrodes.

SUMMARY

The present disclosure may comprise one or more of the features recited in the attached claims, and/or one or more of the following features and combinations thereof. In one aspect, a non-percutaneous trans-auricular nerve field stimulation device may comprise a first plurality of spaced-apart electrically conductive electrodes each arranged to non-percutaneously contact a ventral aspect of an auricle of a human ear, a second plurality of spaced-apart electrically conductive electrodes each arranged to non-percutaneously contact a dorsal aspect of the auricle, and electrical circuitry coupled to the first and second plurality of electrodes and configured to selectively apply electrical stimulation signals to at least one of the first plurality of electrodes and the second plurality of electrodes to cause a first set of trans-auricular currents to flow through the auricle between the first plurality of electrodes and respective ones of the second plurality of electrodes paired therewith according to a first pairing, and to cause a second set of trans-auricular currents to flow through the auricle between the first plurality of electrodes and respective ones of the second plurality of electrodes paired therewith according to a second pairing different from the first pairing, the first and second sets of trans-auricular currents to stimulate at least one auricular nerve field within the auricle.

In another aspect, a non-percutaneous trans-auricular nerve field stimulation device may comprise a first electrically conductive electrode arranged to non-percutaneously contact a first portion of a ventral aspect of an auricle of a human ear, a second electrically conductive electrode arranged to non-percutaneously contact a first portion of a dorsal aspect of the auricle opposite the first portion of the ventral aspect, a third electrically conductive electrode arranged to non-percutaneously contact a second portion of the ventral aspect of auricle spaced apart from the first portion of the ventral aspect, a fourth electrically conductive electrode arranged to non-percutaneously contact a second portion of the dorsal aspect of the auricle opposite the second portion of the ventral aspect, and electrical circuitry coupled to the first, second third and fourth electrodes, the electrical circuitry configured to (i) selectively apply a first electrical stimulation signal to at least one of the first and second electrodes to cause a first trans-auricular current to flow therebetween and transversely through the auricle in a direction parallel to a transverse plane of the auricle, (ii) selectively apply a second electrical stimulation signal to at least one of the third and fourth electrodes to cause a second trans-auricular current to flow therebetween and transversely through the auricle in the direction parallel to the transverse plane of the auricle, (iii) selectively apply a third electrical stimulation signal to at least one of the second and third electrodes to cause a third trans-auricular current to flow therebetween and diagonally through the auricle, and (iv) selectively apply a fourth electrical stimulation signal to at least one of the first and fourth electrode to cause a fourth trans-auricular current to flow therebetween and diagonally through the auricle.

In a further aspect, a non-percutaneous trans-auricular nerve field stimulation device may comprise a first electrically conductive electrode arranged to non-percutaneously contact a ventral aspect of an auricle of a human ear, a second electrically conductive electrode arranged to non-percutaneously contact a dorsal aspect of the auricle opposite the first electrically conductive electrode, a third electrically conductive electrode arranged to non-percutaneously contact the ventral aspect of auricle spaced apart from the first electrically conductive electrode, a fourth electrically conductive electrode arranged to non-percutaneously contact the dorsal aspect of the auricle opposite the third electrically conductive electrode, and electrical circuitry coupled to the first, second third and fourth electrodes, the electrical circuitry configured to (i) selectively apply a first electrical stimulation signal of a first frequency to at least one of the first and fourth electrode to cause a first trans-auricular current to flow therebetween and diagonally through the auricle, and (ii) selectively apply a second electrical stimulation signal of a second frequency, different than the first frequency, to at least one of the second and third electrodes to cause a second trans-auricular current to flow therebetween and diagonally through the auricle, wherein the first and second trans-auricular currents define an interferential current within the auricle.

BRIEF DESCRIPTION OF THE DRAWINGS

This disclosure is illustrated by way of example and not by way of limitation in the accompanying Figures. Where considered appropriate, reference labels have been repeated among the Figures to indicate corresponding or analogous elements.

FIG. 9A is a side elevational view of an embodiment of a hybrid electrode assembly having a non-percutaneous electrode surrounding a percutaneously insertable needle electrode.

FIG. 9B is a perspective view of the hybrid electrode assembly of FIG. 9A.

FIG. 10 is a plan view of a human ear demonstrating an example placement of multiple ones of the hybrid electrode assemblies of FIGS. 9A and 9B.

DETAILED DESCRIPTION OF THE DRAWING

Figure 1:
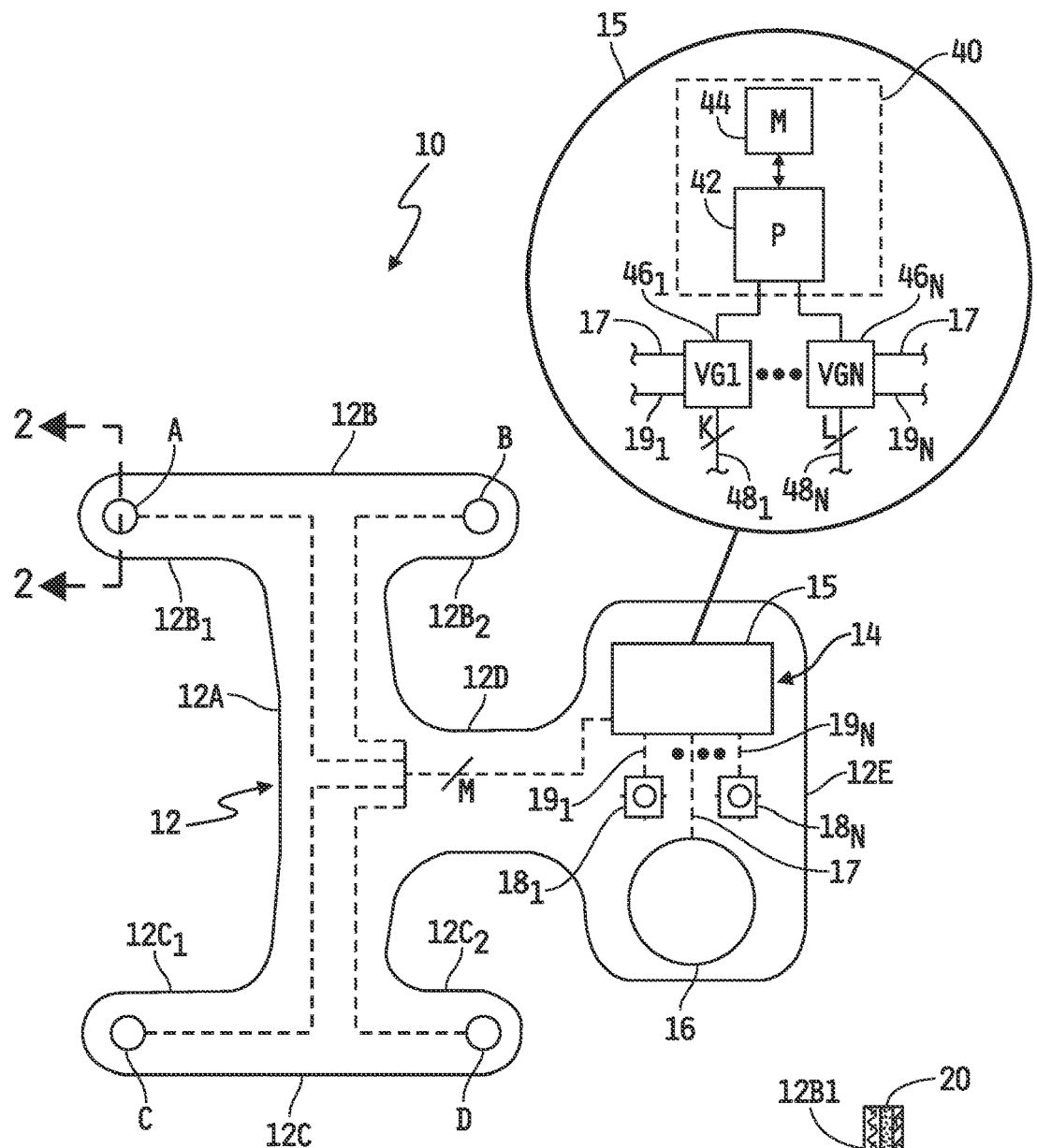
FIG. 1 is a side elevational view of an embodiment of a non-percutaneous trans-auricular nerve field stimulation device.

While the concepts of the present disclosure are susceptible to various modifications and alternative forms, specific exemplary embodiments thereof have been shown by way of example in the drawing and will herein be described in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases may or may not necessarily refer to the same embodiment. Further, when a particular feature, structure or characteristic is described in connection with an embodiment, it is submitted that it is within the knowledge of one skilled in the art to effect such feature, structure or characteristic in connection with other embodiments whether or not explicitly described. Further still, it is contemplated that any single feature, structure or characteristic disclosed herein may be combined with any one or more other disclosed feature, structure or characteristic, whether or not explicitly described, and that no limitations on the types and/or number of such combinations should therefore be inferred.

The present disclosure is directed to a device and method using at least two non-percutaneous electrodes mounted in contact with the skin of the dorsal aspect of a human or animal auricle and at least two non-percutaneous electrodes mounted in contact with the skin of the ventral aspect of the same auricle. Electrical stimulation signals are selectively applied to the electrodes to direct current flow in multiple directions through the auricle to effectuate trans-auricular, multi-directional peripheral nerve field stimulation within the auricle.

Definitions

For purposes of this disclosure, the following terms are defined. Like terms recited in the appended claims are to be interpreted consistently with the following terms:

Auricle—the visible portion of a human or animal hear residing outside of the human or animal head.

Dorsal aspect—rear surface of the auricle.

Ventral aspect—front surface of the auricle.

Coronal plane of the auricle—a plane dividing the auricle into the dorsal and ventral aspects.

Transverse plane of the auricle—a plane passing through the dorsal and ventral aspects of auricle, perpendicular to the coronal plane of the auricle, and dividing the auricle into top and bottom portions.

Trans-auricular—transversely through the auricle from the dorsal aspect to the ventral aspect and/or vice versa.

Trans-auricular current—current passing transversely through the auricle from the dorsal aspect to the ventral aspect and/or vice versa.

Non-percutaneous(ly) contact or contacting—physically contacting but not penetrating, piercing or otherwise breaking the skin.

Percutaneous insertion—penetrating or piercing the skin.

Interferential current—as between four electrodes placed on the auricle with two spaced apart along the ventral aspect and the remaining two spaced apart along the dorsal aspect, and with a current having a first frequency established diagonally through the auricle between one ventral electrode and a spaced apart one of the dorsal electrodes and another current having a second frequency established diagonally through the auricle between the other ventral electrode and the spaced apart other dorsal electrode, an interferential current in a space within the auricle intersected by the two currents has a frequency equal to the difference between the first and second frequencies.

First Embodiment

Referring to FIGS. 1-4, an embodiment is shown of a non-percutaneous trans-auricular nerve field stimulation device 10. The device 10 includes multiple non-percutaneous electrodes, e.g., A, B, C and D in the embodiment illustrated in FIGS. 1-4, and electrical circuitry, e.g., circuitry 14 illustrated in FIGS. 1 and 3, for generating electrical stimulation signals and supplying the generated electrical stimulation signals to the electrodes. The electrodes are non-percutaneous in that they are configured to be positioned in contact the surface of the skin but not to pierce, penetrate or otherwise break through the surface of the skin, and electrical circuitry for generating and applying electrical stimulation signals to the electrodes. The electrodes are also electrically conductive and serve to deliver the electrical stimulation signals to the tissues within the auricle via contact with the skin surfaces of the ventral and dorsal aspects of the auricle as will be described in greater detail below. In one example embodiment, the electrodes are provided in the form of a low-resistance, high electrical conductivity, high-density silicone connecters such as those commercially available from Fujipoly America Corp. of Carteret, New Jersey under the trade name ZEBRA® Elastomeric Electronic Connectors. In alternate embodiments, one or more of the electrodes may be provided in the form of rigid, semi-rigid or flexible electrodes made from or including one or more electrically conductive materials, examples of which include, but are not limited to, copper, aluminum, gold, silver, platinum, palladium, beryllium, nickel, tungsten, titanium, stainless steel, or the like. In some embodiments, the material(s) used to form the electrodes may be restricted, for example, to omit or minimize common allergy-causing materials such as nickel. In some embodiments, low-resistance contact between one or more of the electrodes A, B, C, D and the skin of the auricle 30 may be enhanced by providing conventional electrically conductive gel or other electrically conductive substance on the skin of the auricle 30 and/or on the surface(s) of one or more of the electrodes A, B, C, D prior to making contact between the electrodes and the auricle 30.

Figure 2:
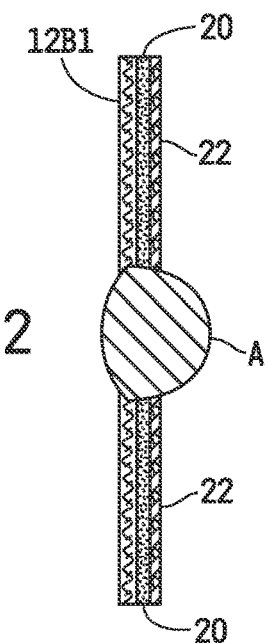
FIG. 2 is a cross-sectional view of the device of FIG. 1 as viewed along section lines 2-2.
Figure 3:
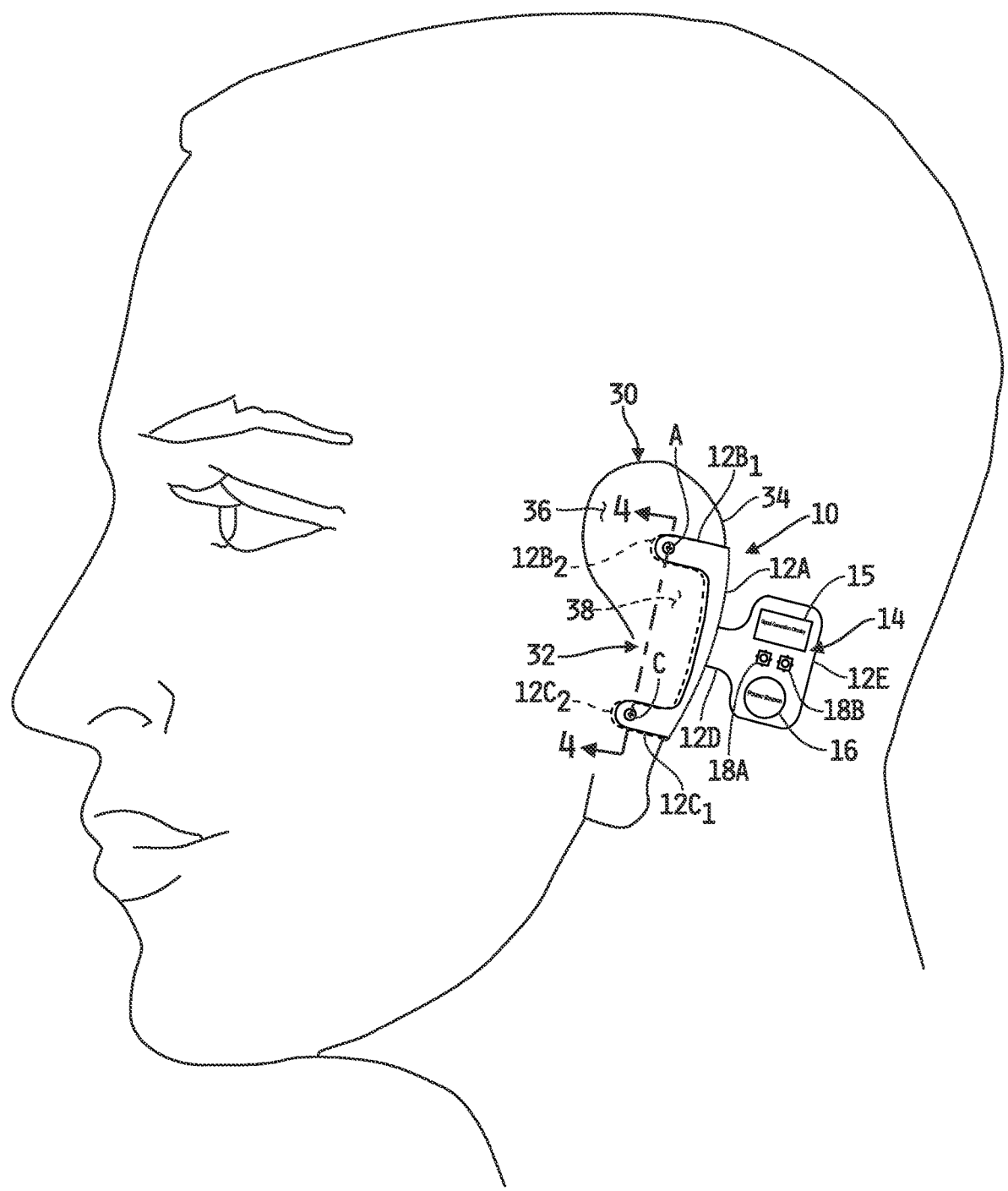
FIG. 3 is a side-elevational view of the device of FIGS. 1 and 2 mounted to ventral and dorsal aspects of an auricle of a human ear.

In some embodiments, the electrodes, e.g., A, B, C and D depicted in FIGS. 1-4, and the electrical circuitry, e.g., 14 depicted in FIGS. 1 and 3, are mounted to or otherwise carried by a flexible (or semi-flexible) carrier 12 configured to be operatively attached to an auricle of a human or animal. In the illustrated embodiment, the flexible carrier 12 is specifically shaped for operative attachment to an auricle 30 of a human, although it will be understood that alternative shapes for attachment to human ears and/or other shapes specific to one or more animal ears are intended to fall within the scope of this disclosure. In the embodiment illustrated in FIGS. 1 and 3, the flexible carrier 12 illustratively includes an elongated main body portion 12A which is sized and configured to extend longitudinally along at least a portion of a helix 34 of an auricle 30 of a human ear 32 and to wrap transversely at least partially about that portion of the helix 34 as illustrated most clearly in FIG. 3.

An upper wing member 12B is defined at an upper or top end of the elongated main body 12A and a lower wing member 12C is defined at a lower end of body 12A. The upper wing member 12B is sized to extend over at least a first portion of the ventral aspect 36 of the auricle 30 and to extend over at least a first portion of the dorsal aspect 38. In this regard, the upper wing member 12B includes a first wing $12B_1$ which extends transversely away from the corresponding upper end of the main body 12A in one direction, e.g., a forward direction, and a second wing $12B_2$ extending transversely away from the corresponding upper end of the main body 12A in an opposite direction, e.g., a rearward direction. The first wing $12B_1$ is configured to extend over and attach to the first portion of the ventral aspect 36, and the second wing $12B_2$ is configured to extend over and attach to the first portion of the dorsal aspect 38, with the upper wing member 12B wrapped around the helix 34 and attached to the helix 34 between the first and second wings $12B_1$, $12B_2$ as illustrated in FIG. 3.

One of the electrodes A is illustratively mounted to the first wing $12B_1$ and another of the electrodes B is mounted to the second wing $12B_2$. At least a portion of the electrode A is exposed at the bottom surface of the first wing $12B_1$, as illustrated by example in FIG. 2, such that the electrode A contacts, and remains in contact with, the skin of the first portion of the ventral aspect 36 of the auricle 30 when the upper wing 12B is attached to the first portion of the ventral aspect 36 of the auricle 30. Likewise, at least a portion of the electrode B is exposed at the bottom surface of the second wing $12B_2$ such that the electrode B contacts, and remains in contact with, the skin of the first portion of the dorsal aspect 38 of the auricle 30 when the upper wing 12B is attached to the first portion of the dorsal aspect 38 of the auricle 30. It is to be understood that the first portion of the ventral aspect 36 to which the electrode A makes contact may be or include any portion of the ventral aspect 36 including, but not limited to, the scapha, the antihelical fold, the antihelix, the upper crus of the antihelix, the lower crus of the antihelix, the triangular fossa, the concha, the crux of the helix and the concha and the concha cava, as these anatomical terms are generally understood. The first portion of the dorsal aspect 38 to which the electrode B makes contact may be or include any portion of the dorsal aspect 38 that is generally opposite (transversely) the portion of the ventral aspect 36 to which the electrode A is disposed in contact.

A lower wing member 12C is defined at a lower or bottom end of the elongated main body 12A opposite the upper or top end of the main body 12A. The lower wing member 12C is sized to extend over at least a second portion of the ventral aspect 36 of the auricle 30 and to extend over at least a second portion of the dorsal aspect 38. In this regard, the lower wing member 12C includes a first wing $12C_1$ which extends transversely away from the corresponding lower end of the main body 12A in the same direction as that of the first wing $12B_1$ of the upper wing member 12B, and a second wing $12C_2$ extending transversely away from the corresponding lower end of the main body 12A in an opposite direction, i.e., in the same direction as that of the second wing $12B_2$ of the upper wing member 12B.

The first wing $12B_1$ is configured to extend over and attach to the first portion of the ventral aspect 36, and the second wing $12B_2$ is configured to extend over and attach to the first portion of the dorsal aspect 38, with the upper wing member 12B wrapped around the helix 34 and attached to the helix 34 between the first and second wings $1261$, $12B_2$ as illustrated in FIG. 3. The electrode C is illustratively mounted to the first wing $12C_1$ and the electrode D is mounted to the second wing $12C_2$. At least a portion of the electrode C is exposed at the bottom surface of the first wing $12C_1$ such that the electrode C contacts, and remains in contact with, the skin of the second portion of the ventral aspect 36 of the auricle 30 when the lower wing 12C is attached to the second portion of the ventral aspect 36 of the auricle 30. Likewise, at least a portion of the electrode D is exposed at the bottom surface of the second wing 12C$_2$ such that the electrode D contacts, and remains in contact with, the skin of the second portion of the dorsal aspect 38 of the auricle 30 when the lower wing 12C is attached to the second portion of the dorsal aspect 38 of the auricle 30. The second portion of the ventral aspect 36 to which the electrode C makes contact may be or include any portion of the ventral aspect 36 below that to which the electrode A makes contact. Depending upon the area of the ventral aspect 36 to which the electrode A makes contact, which may illustratively vary from application to application, may be or include any suitable remaining portion of the ventral aspect 36 including, but not limited to, the scapha, the antihelical fold, the antihelix, the upper crus of the antihelix, the lower crus of the antihelix, the triangular fossa, the concha, the crux of the helix, the concha and the concha cava. The second portion of the dorsal aspect 38 to which the electrode D makes contact may be or include any portion of the dorsal aspect 38 that is generally opposite (transversely) the portion of the ventral aspect 36 to which the electrode D is disposed in contact.

The carrier 12 further includes an electrical circuit mounting portion 12E to which electrical circuitry 14 is mounted, as will be described in detail below, and a circuit extension member 12D between the main body 12A and the electrical circuit mounting portion 12E. Illustratively, the circuit extension member 12D extends rearwardly from a portion the main body 12A between the upper and lower wing members 12B, 12C, e.g., in the same directions as the wings 12B$_2$ and 12C$_2$, and the electrical circuit mounting portion 12E is thus likewise rearward relative to the main body 12A. In alternate embodiments, the electrical circuit mounting portion 12E may extend from other portions of the main body 12A. In any case, a number, M, of electrical conductors extend along the various portions of the carrier 12 to electrically connect each of the electrodes A, B, C and D to the electrical circuitry 14. M may be any positive integer. In some embodiments, one or more, or all, of the electrical conductors are embedded within the carrier 12, and in other embodiments one or more, or all, of the electrical conductors are attached to the top or bottom surface of the carrier 12.

As illustrated by example in FIG. 2, an adhesive layer 20 may cover all or one or more portions of the bottom surface of the carrier 12 for the purpose of attaching, e.g., affixing, the carrier 12 to the auricle 30 as illustrated in FIG. 3 and described above. In some such embodiments, a removable layer 22, such as paper or other such layer, may cover the adhesive layer 20 to protect the adhesive layer 20 prior to application. The removable layer 22, in embodiments which include it, is to be removed prior to attachment of the carrier 12 to the auricle 30 as illustrated in FIG. 3. It will be appreciated that the adhesive layer 20 illustrated in FIG. 2 represents only one example structure and technique for attaching the flexible carrier 12 to the auricle 30, and that this disclosure contemplates alternatively or additionally using one or more other conventional structures and techniques for attaching, affixing, mounting or otherwise securing the flexible carrier 12 to the auricle 30. In one example embodiment, the carrier 12 is provided in the form of a woven fabric material, although this disclosure contemplates alternate embodiments in which the carrier 12 may be or include, but should not be limited to, a non-woven fabric, one or more other woven or non-woven textiles, latex or one or more suitable plastic materials such as polyvinylchloride (PVC), polyethylene, and/or polyurethane.

Referring now specifically to FIG. 1, the electrical circuitry 14 mounted to or otherwise carried by the electrical circuit mounting portion 12E of the carrier 12 illustratively includes signal generation circuitry 15 and at least one power source 16 electrically connected to the signal generation circuitry 14 via at least one corresponding electrical conductor 17. In some embodiments, the electrical circuitry 14 further illustratively includes a number, N, of voltage adjustment switches $18_1$-$18_N$, electrically connected to the signal generation circuitry 14 via a corresponding number, N, of electrical conductors $19_1$-$19_N$, where N may be any positive integer. The signal generation circuitry 15 is configured and operable, as will be described in greater detail below, to selectively apply electrical stimulation signals to one or more of the electrodes A, B, C, D to cause one or more trans-auricular currents to flow through the tissue of the auricle 30 between one or more of the electrodes A, B in contact with the ventral aspect 36 and one or more of the electrodes C, D in contact with the dorsal aspect 38 so as to stimulate one or more auricular nerve fields within the auricle 30.

As further illustrated in FIG. 1, an embodiment of the signal generation circuitry 14 illustratively includes at least one control circuit 40 electrically coupled to the at least one power source 16 and to any number, N, conventional gating circuits $46_1$-$46_N$, wherein N may be any positive integer as described above. In one embodiment, the at least one control circuit 40 is illustratively provided in the form of at least one conventional processor or controller 42 communicatively coupled to a conventional memory 44, wherein the memory 44 has instructions, i.e., one or more programs, stored therein which, when executed by the processor or controller 42, cause the processor or controller 42 to generate electrical stimulation control signals which are provided to the one or more gating circuits $46_1$-$46_N$. The one or more gating circuits $46_1$-$46_N$ is/are, in turn, responsive to the electrical stimulation control signals produced by the processor or controller 42 to produce the electrical stimulation signals to be applied to one or more of the electrodes A, B, C, D using electrical power produced by the at least one power source 16. In alternate embodiments, the at least one control circuit 40 may be provided in other forms such as one or a combination of analog and/or digital hardware circuits.

The one or more gating circuits $46_1$-$46_N$ are illustratively controlled by the at least one control circuit 40 to selectively apply voltages to one or more of the electrodes A, B, C, D as will be described in greater detail below. In some embodiments, the at least one control circuit 40 may include the one or more gating circuits $46_1$-$46_N$. In some embodiments, one or more voltage adjustment switches $18_1$-$18_N$, e.g., one for each gating circuit, is/are provided to allow adjustment of the maximum and/or minimum voltage(s) produced by the gating circuits. Illustratively, such gating circuit(s), in embodiments which include it/them, may be provided in the form of conventional pressure sensitive voltage adjustment switches, although other conventional voltage adjustment switches or actuators may alternatively be used. In any case, one or more of the voltage adjustment switches $18_1$-$18_N$ may be configured and/or modified in one embodiment so as to be adjusted only during manufacturing and/or subsequent testing, and in other embodiments one or more of the voltage adjustment switches $18_1$-$18_N$ may be configured and/or modified so as to be adjustable by the user and/or person(s) assisting the user.

In the embodiment illustrated in FIG. 1, a single power source 16 is shown mounted to or otherwise carried by the carrier 12. In one embodiment, the power source 16 is a DC power source, e.g., illustratively provided in the form of a conventional battery. In other embodiments, the power source 16 may be or include one or more other conventional AC and/or DC voltage and/or current sources or storage devices. In some embodiments, two or more power sources 16 of any type may be included. In embodiments which include only a single power source 16 as shown, the single power source 16 supplies electrical power to all electrical power consuming circuits including the one or more gating circuits $18_1$-$18_N$. In some embodiments which include two or more such gating circuits, the signal generation circuitry 14 may be configured such that all such gating circuits illustratively share a common electrical power reference potential, e.g., ground reference. In other embodiments which include two or more gating circuits, the signal generation circuitry 14 may be configured such that the electrical power references of at least two of the gating circuits are decoupled from one another. In any case, the circuit components of the signal generation circuitry 15 is/are illustratively operable, e.g., programmed, electrically interconnected and/or otherwise configured, to control one or more attributes of one or more of the electrical stimulation signals provided to one or more of the electrodes A, B, C, D. Examples of such attributes may be or include, but should not be limited to, switching frequency, duty cycle, signal duration, pause time between signal applications, maximum and/or minimum voltage level, maximum and/or minimum current level, polarity of voltage applied across two or more of the electrodes, signal sequence application duration and overall therapy duration in which at least one electrical stimulation signal is produced.

Figure 4:
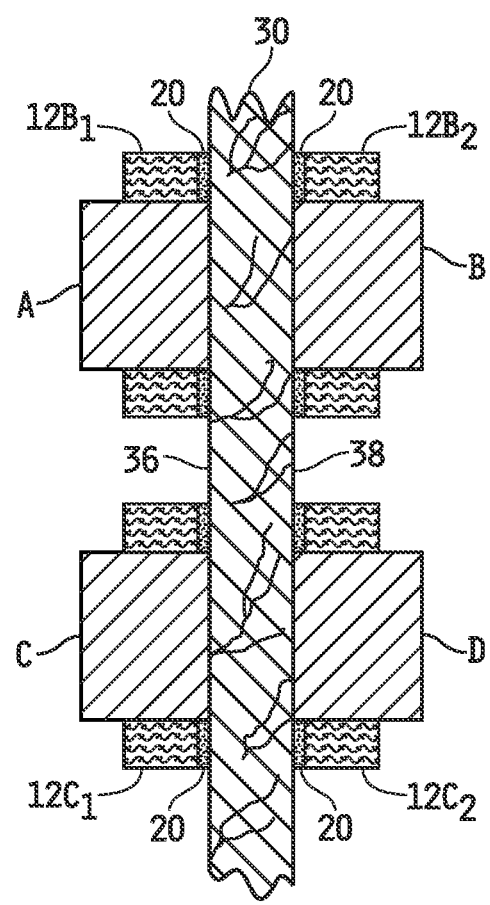
FIG. 4 is a cross-sectional view of the device illustrated in FIG. 3 as viewed along section lines 4-4.

Referring now to FIG. 4, a cross-sectional diagram is shown as viewed along section lines 4-4 of FIG. 3. As illustrated in FIG. 4, the carrier 12 is attached to the auricle 30, e.g., via an adhesive layer 20, such that the electrodes A and C are in contact with the skin surface of the ventral aspect 36 of the auricle 30 and are spaced apart from one another along the ventral aspect 36, and such that the electrodes B and D are similarly in contact with the skin surface of the dorsal aspect 38 of the auricle 30 and are spaced apart from one another along the dorsal aspect 38. The electrode B is illustratively aligned with the electrode A and the electrode D is illustratively aligned with the electrode C. The illustrated arrangement is preferred but not strictly required as, in practice, the electrodes A, B and or the electrodes C, D may be somewhat offset relative to one another. In either case, the electrodes A, B, C, D are arranged to be responsive to electrical stimulation signals supplied thereto to cause trans-auricular current to flow through the auricle 30, in either direction, between electrodes A and B, between electrodes C and D, between electrodes A and D and between electrodes B and C. As will be described in greater detail below, the electrical stimulation signals may be controlled to cause only one such trans-auricular current to flow through the auricle 30 at any one time, to cause any combination of such trans-auricular currents to simultaneously flow through the auricle 30 and/or to cause a sequence of any such trans-auricular current(s) to flow through the auricle 30 over time and/or a sequence of times.

Figure 5:
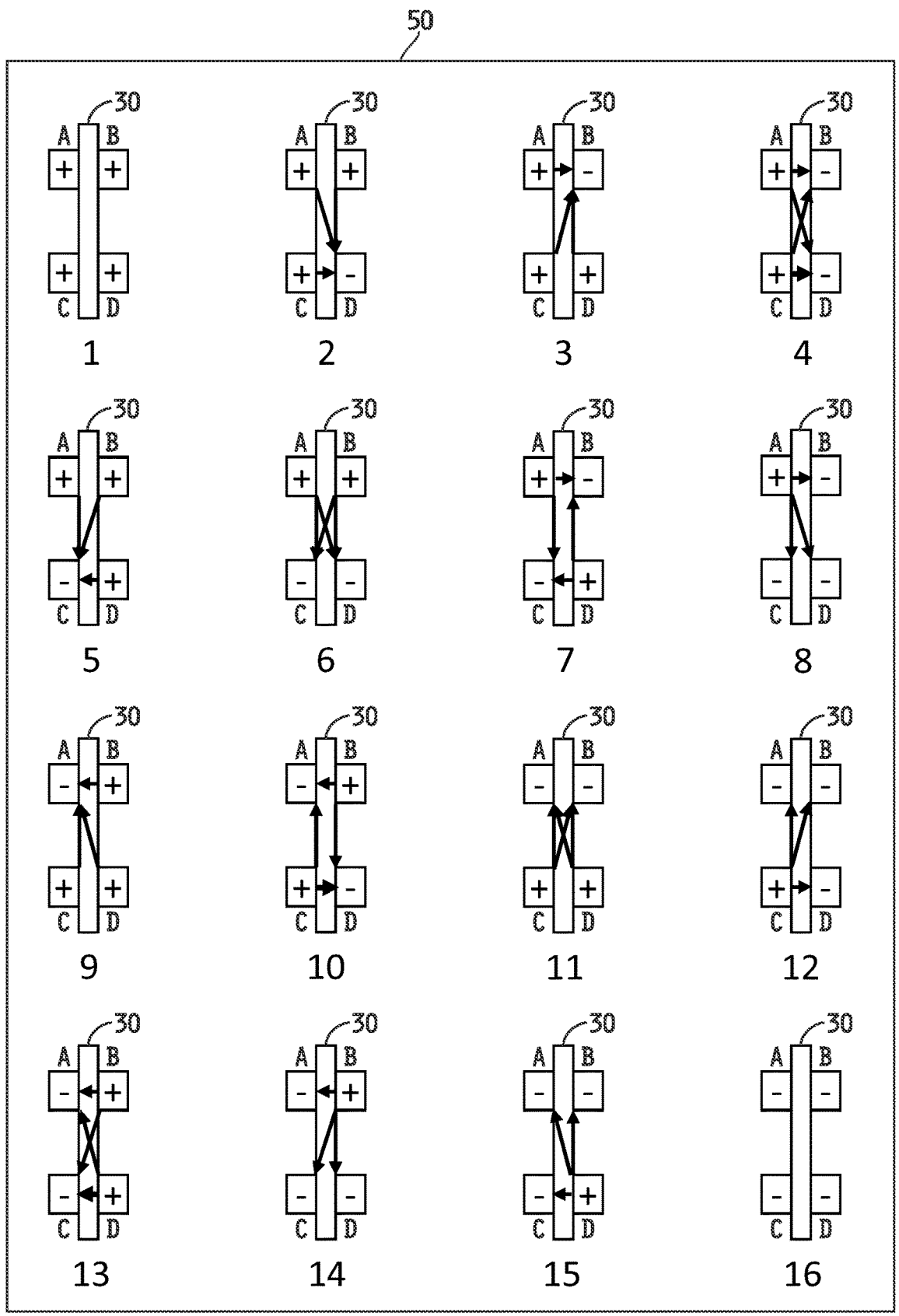
FIG. 5 is a table illustrating the possible combinations of trans-auricular current flow between the four electrodes of the device illustrated in FIGS. 1-4 using a single voltage gating circuit or multiple voltage gating circuits with common ground references.

Referring now to FIG. 5, a table 50 is shown of all possible voltage polarity combinations that could be applied to the electrodes A, B, C, D using at least one DC voltage source 16. As there are four such electrodes A, B, C, D, there are $2^4$=16 possible combinations. Indeed, in embodiments which include K electrodes, where K is any positive, and typically even, integer, the total number of possible voltage polarity combinations that could be applied to such electrodes is 2K. The arrow-tipped lines represent the directions of current flow through the auricle 30 in response to the applied voltages. It is evident from these depictions that the voltages applied to the electrodes A, B, C, D are applied simultaneously, and are physically applied either by a single gating circuit 46 or by multiple gating circuits sharing a common electrical power source reference. Only polarity combinations 1 and 16 fail to produce current flow, and the remaining combinations result in current flow through the auricle 30 in a direction parallel to the transverse plane of the auricle 30, e.g., the two through-currents depicted in polarity combination 7, current flow through the auricle 30 diagonally between electrodes A, D and/or B, C, e.g., the two diagonal currents depicted in polarity combination 6, and/or current flow along the skin, and at least partially into the auricle tissue, of the ventral aspect 36 and/or the dorsal aspect 38, e.g., the current flowing between electrodes A and C along the skin surface of the ventral aspect 36 and the current flowing between electrodes D and B along the skin surface of the dorsal aspect 38, as depicted in polarity combination 7.

Figure 6:
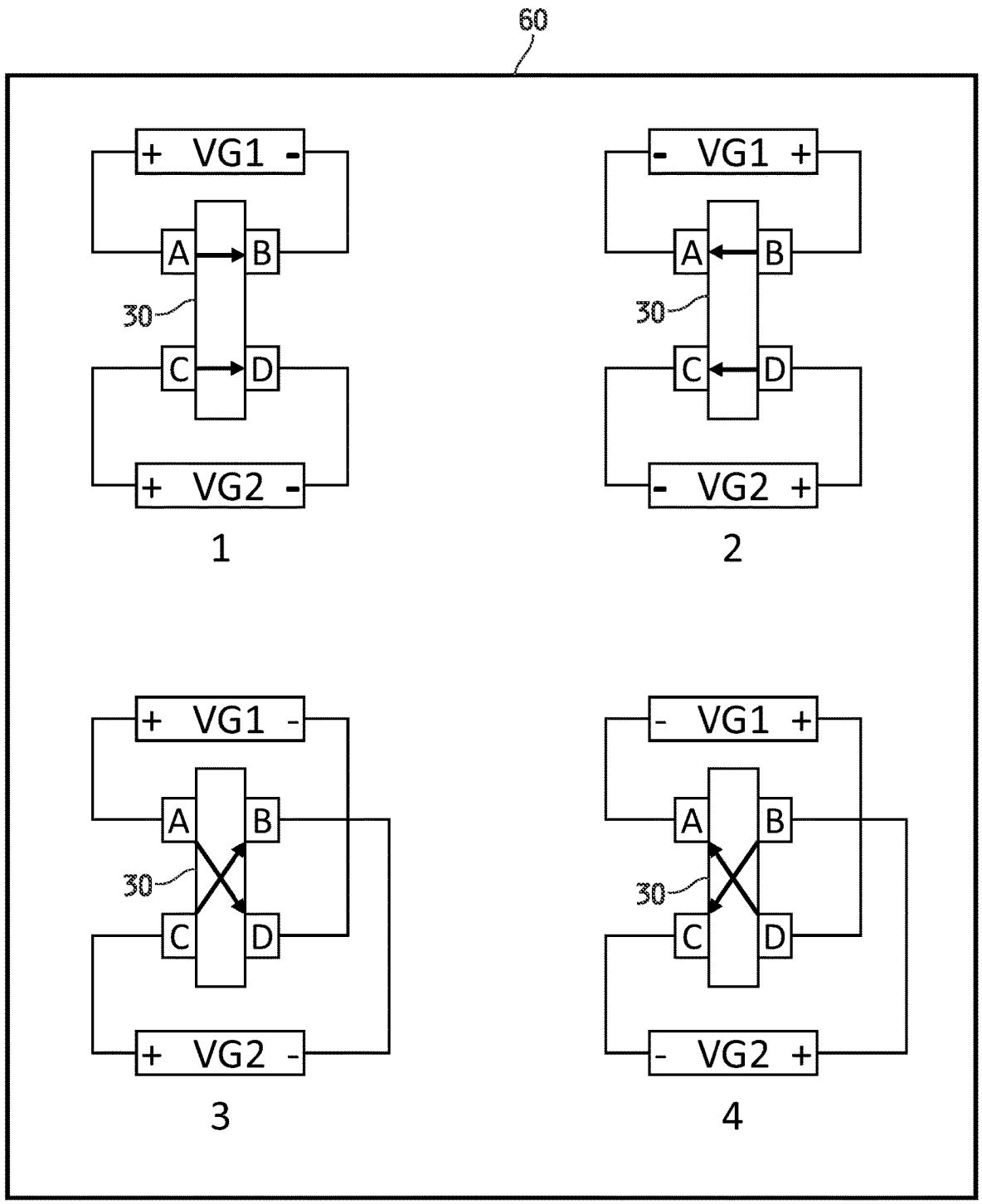
FIG. 6 is another table illustrating some of the possible combinations of trans-auricular current flow between the four electrodes of the device illustrated in FIGS. 1-4 using two voltage gating circuits with decoupled ground references.

As described above, it is also possible to decouple the power source references of two or more gating circuits which apply electrical stimulation pulses to the electrodes A, B, C, D. Such an arrangement effectively modifies the current flow possibilities depicted in FIG. 5 by directing current flow only between specifically paired ones of the electrodes A, B, C, D. Referring to FIG. 6, for example, a table 60 is shown depicting four possible trans-auricular current flow scenarios using two reference (ground) decoupled gating circuits VG1 and VG2. In gating combination 1, a positive voltage is applied by VG1 between electrodes A and B, and a separate (i.e., decoupled) positive voltage is simultaneously applied by VG2 between electrodes C and D. The result is the simultaneous flow of a first trans-auricular current through the auricle 30 from electrode A toward electrode B, and a second trans-auricular current through the auricle 30 from electrode C toward electrode D. Both such currents flow in a direction that is parallel to the physiological transverse plane of the auricle 30. In gating combination 2, the polarities of the VG1 and VG2 are reversed, resulting in the flow of the same first and second trans-auricular currents but in the opposite direction as those depicted in gating combination 1.

In gating combination 3, a positive voltage is applied by VG1 between electrodes A and D, and a separate (i.e., decoupled) positive voltage is simultaneously applied by VG2 between electrodes C and B. The result is the simultaneous flow of a third trans-auricular current through the auricle 30 from electrode A toward electrode D, and a fourth trans-auricular current through the auricle 30 from electrode C toward electrode B. The third trans-auricular current flows through the auricle 30 in a downward diagonal direction between electrodes A and D and the fourth trans-auricular current flows through the auricle 30 in a downward diagonal direction between the electrodes C and B. In gating combination 4, the polarities of the VG1 and VG2 are reversed, resulting in the flow of the same third and fourth trans-auricular currents but each in opposite directions as those depicted in gating combination 3.

As is evident from FIGS. 5 and 6, various trans-auricular current flows can be established by controllably and selectively pairing the electrodes A and C contacting the ventral aspect 36 of the auricle 30 with different ones of the electrodes B and D contacting the dorsal aspect 38, and then further controlling the polarities of the applied voltages to control trans-auricular current flow direction. Using the gating combinations illustrated in FIG. 6 as one example, VG1 and VG2 are set in gating combinations 1 and 2 to a first pairing in which electrode A is paired with electrode B and in which electrode C is paired with electrode D. In gating combinations 3 and 4, VG1 and VG2 are set to a second pairing in which electrode A is paired with electrode D and in which electrode B is paired with electrode C. Electrical stimulation signals generated by the electrical circuitry 14 are then applied to the different pairings, e.g., one pairing after the other to cause a first set of trans-auricular currents to flow through auricle 30, e.g., using gating combinations 1 and/or 2, and to then cause a second set of trans-auricular currents to flow through the auricle 30, e.g., using gating combinations 3 and/or 4. Such applications of the electrical generation signals can be applied sequentially, i.e., such that one set of trans-auricular current flows but not the other and then vice versa, or simultaneously using gating circuits that share a common reference potential, e.g., ground reference, as illustrated in FIG. 5, or using gating circuits having decoupled references, e.g., ground references, as illustrated in FIG. 6.

It should be apparent from the foregoing description that the electrical circuit 14 may be programmed or otherwise configured to selectively apply electrical stimulation signals, e.g., in the form of voltage or voltage differentials, to various combinations of the electrodes A, B, C, D, simultaneously and/or sequentially and with any desired signal attributes as described above, for the purpose of causing corresponding trans-auricular currents to flow through the auricle 30 to provide therapy by stimulating at least one auricular nerve field within the auricle 30. One example sequence of such electrical stimulation signals for providing auricular nerve field stimulation is the following, although those skilled in the art will recognize that this sequence represents only one of many different possible therapy approaches that may be implemented using the device 10. It will be understood that all such different therapy approaches implementable using the device 10 are intended to fall within the scope of this disclosure. In any case, the following example sequence will assume the use of two ground reference-decoupled gating circuits controllable to selectively apply voltages and voltage differentials to the electrodes A, B, C, D as illustrated in FIG. 6.

Example Therapy Sequence

The following pattern of items 1-16 is illustratively repeated sequentially for P time units with a rest or pause time between each repeated pattern (in which no electrical stimulation signals are applied) of Q time units. The total therapy time is R time units.

1. Apply S volts according to combination 1 at T hertz for U time units.
2. Rest or pause V time units.
3. Apply S volts according to combination 2 at T hertz for U time units.
4. Rest or pause V time units.
5. Apply S volts according to combination 1 at W hertz for U time units.
6. Rest or pause V time units.
7. Apply S volts according to combination 2 at W hertz for U time units.
8. Rest or pause V time units.
9. Apply S volts according to combination 3 at T hertz for U time units.
10. Rest or pause V time units.
11. Apply S volts according to combination 4 at T hertz for U time units.
12. Rest or pause V time units.
13. Apply S volts according to combination 3 at W hertz for U time units.
14. Rest or pause V time units.
15. Apply S volts according to combination 4 at W hertz for U time units.
16. Rest or pause V time units.

Example values of variables P-W are the following, although it will be understood that in other implementations one or more of P-W may take on different values:

P=15 minutes.
Q=1 minute.
R=72 hours.
S=4.2 volts.
T=1 Hz.
U=1 millisecond.
V=2000 milliseconds.
W=10 Hz.

It will be further understood that in some embodiments one or more of the items 1-16 may be omitted and/or executed at a different point in the pattern, such that the sequential pattern may include any combination of any of items 1-16 executed in any order. In some alternate embodiments, the voltage applied between electrodes A and D in any or all of steps 9, 11, 13 and 15 may have a different frequency than the voltage applied between electrodes B and C so as to establish an interferential current in a space within the auricle 30 intersected by the two currents flowing between the pairs A, D and B, C of the four electrodes A, B, C and D.

Second Embodiment

Figure 7:
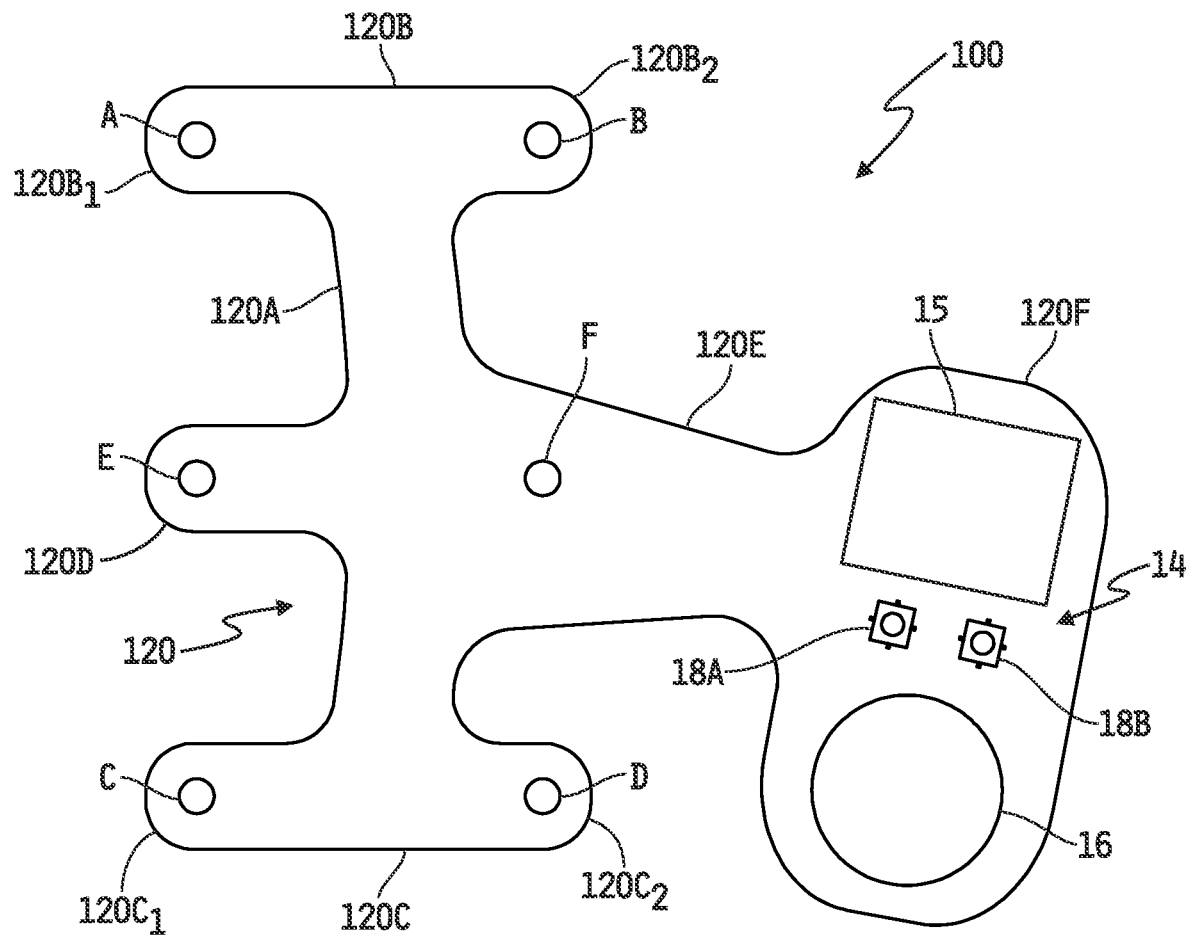
FIG. 7 is a side elevational view of another embodiment of a non-percutaneous trans-auricular nerve field stimulation device.
Figure 8:
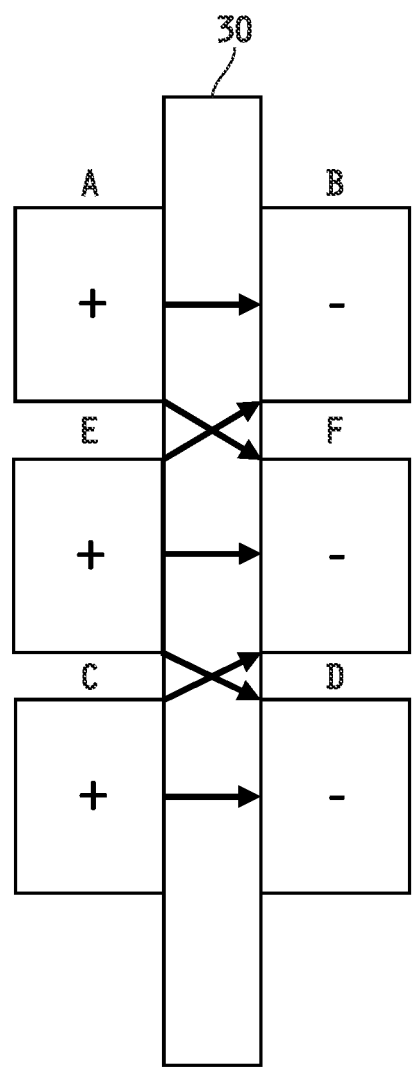
FIG. 8 is a simplified diagram illustrating one example trans-auricular current flow between the six electrodes of the device illustrated in FIG. 7 using voltage gating circuits with common ground references.

The first embodiment of the non-percutaneous trans-auricular nerve field stimulation device 10 is illustrated in FIGS. 1-6 and described above as including four electrodes A, B, C, D with two electrodes in spaced-apart contact with the ventral aspect 36 of the auricle 30 and with the remaining two electrodes in spaced-apart contact with the dorsal aspect 38. It will be understood, however, that no limit on the total number of electrodes and/or electrode pairs is intended or should be inferred. In this regard, a second embodiment of a non-percutaneous trans-auricular nerve field stimulation device 100 is illustrated in FIGS. 7 and 8 which includes a total of 6 electrodes A-F with three of the electrodes A, E and C in spaced-apart contact with the ventral aspect 36 of the auricle 30 and with the remaining three electrodes B, F and D in spaced-apart contact with the dorsal aspect 38. The carrier 120, like the carrier 12 illustrated in FIGS. 1-3, includes a main body 120A, an upper wing member 120B defining first and second wings 120B$_1$ and 120B$_2$ to which the electrodes A and B are respectively mounted, a lower wing member 120C defining first and second wings 120C$_1$ and 120C$_2$ to which the electrodes C and D are respectively mounted, an electrical circuit mounting portion 120F to which the electrical circuitry 14 is mounted and a circuit extension member 120E between the main body 120A and the electrical circuit mounting portion 120F. Unlike the carrier 12 illustrated in FIGS. 1-3, the carrier 120 further includes a middle wing 120D extending transversely away from the main body between, and in the same direction as, the wings 120B$_1$ and 120B$_2$. The electrode E is mounted to the middle wing 120D and the electrode F is mounted to the circuit extension member 120F. In the illustrated embodiment, the electrodes A, E and C are respectively aligned with one another transversely about an imaginary longitudinal line bisecting the main body 120A, although it will be understood that such alignment is not strictly required as other possible locations of the electrodes relative to the carrier 120 are contemplated.

With the illustrated electrode arrangement, a total of $2^6=64$ possible combinations of current flow combinations can be realized via selective application of voltage potentials to and between various ones of the electrodes A-F, and in this regard one example combination is illustrated in FIG. 8. As with the device 10 illustrated in FIGS. 1-6, the electrical circuitry 14 may include one or more gating circuits. If multiple gating circuits are included, two or more such gating circuits may share a common reference potential, e.g., ground reference, and/or two or more gating circuits may have decoupled references, e.g., decoupled ground references.

Third Embodiment

The first and second embodiments of the auricular nerve field stimulation device 10 and 100 illustrated in FIGS. 1-6 and 7-8 respectively include four or more non-percutaneous electrodes spaced apart from one another in trans-auricular pairs as described above. A third embodiment replaces at least one of the multiple non-percutaneous, trans-auricular electrode pairs with hybrid, trans-auricular electrode pairs each having at least one non-percutaneously contacting electrode and at least one needle electrode for percutaneous insertion into the auricle 30 of the ear 32. An embodiment of such a hybrid electrode is illustrated in FIGS. 9A and 9B in the form of a hybrid electrode assembly 200.

Referring to FIGS. 9A and 9B, the hybrid electrode assembly 200 includes an electrically non-conductive (i.e., electrically insulating) housing 202 in the form of a generally circular disk having a generally planar surface 214A upon which an electrically conductive ring 204 is formed or attached in a conventional manner, and into which an insulated electrical conductor 206 extends into electrical contact, i.e., attachment, with the ring 204. In the illustrated embodiment, the ring 204 circumscribes the housing 202, although in alternate embodiments the ring 204 may be segmented into two or more pieces each electrically connected to the conductor 206. An outer periphery of the ring 204 is illustratively adjacent to an outer periphery of the circular housing 202, although in alternate embodiments the outer periphery of the ring 204 may be inboard of the outer periphery of the housing 202 such that at least a portion of the surface 214A of the housing 202 extends beyond the outer periphery of the ring 204. In one example implementation, which should not be considered to be limiting in any way, the circular housing 202 has a height or thickness of about 2 millimeters (mm) and a diameter of about 3 mm, although in alternate implementations the height or thickness may be more or less than 2 mm and/or the diameter may be more or less than 3 mm. Moreover, it will be understood that the circular disk configuration of the housing 202 illustrated in FIGS. 9A and 9B is provided only by way of illustration, and that in alternate embodiments the housing 202 may have other shapes or configurations.

A needle housing 208, also illustratively in the form of a generally circular disk, is coupled to a surface 214B of the housing 202 opposite the surface 214A. In one embodiment, the needle housing 208 is separate from the housing 202 and is attached or affixed thereto in a conventional manner, although alternate embodiments are contemplated in which the needle housing 208 is integral with the housing 202 such that the housings 202 and 208 are of unitary construction. In any case, an insulated electrical conductor 212 extends into the needle housing 208 and is electrical connected to an electrically conductive needle or needle electrode 210 carried by the needle housing 208. The needle or needle electrode 210 extends from the needle housing 208 and centrally through the housing 202 such that a portion of the needle 210 extends outwardly away from the surface 214A of the housing 202. As best shown in FIG. 9B, an inner periphery of the electrically conductive ring 204 surrounds the needle electrode 210 with the needle electrode 210 spaced apart from the ring 204 by a ring-shaped portion 216 of the surface 214A of the housing 202. The electrically conductive needle electrode 210 is thus electrically isolated from the electrically conductive ring 204 by the housings 202 and 218, and the electrical conductors 206, 212 are independent from one another with each attached to a respective one of the ring 204 and the needle electrode 210. In the illustrated embodiment, the hybrid electrode assembly 202 carries a single needle electrode 210, although in alternate embodiments the needle electrode 210 may be augmented with one or more additional needle electrodes each electrically connected to the electrical conductor 212.

In some embodiments, at least one trans-auricular pair of non-percutaneous electrodes illustrated in FIGS. 1-8 may be replaced by a pair of the hybrid electrode assemblies 200 likewise placed in a trans-auricular relationship relative to one another with the needle electrodes 210 thereof percutaneously inserted into the auricle 30 and advanced therein until the electrically conductive rings 204 thereof non-percutaneously contact the skin about the respective needle electrodes 210. In some such embodiments, all of the trans-auricular pairs of non-percutaneous electrodes illustrated in FIGS. 1-8 may be replaced by corresponding pairs of the hybrid electrode assemblies 200. In other embodiments, the hybrid electrode assemblies 200 may be placed, in trans-auricular pairs, at locations or positions along the auricle 30 different from that illustrated in FIG. 3, as can the non-percutaneous electrodes illustrated in FIGS. 1-8.

Figure 11:
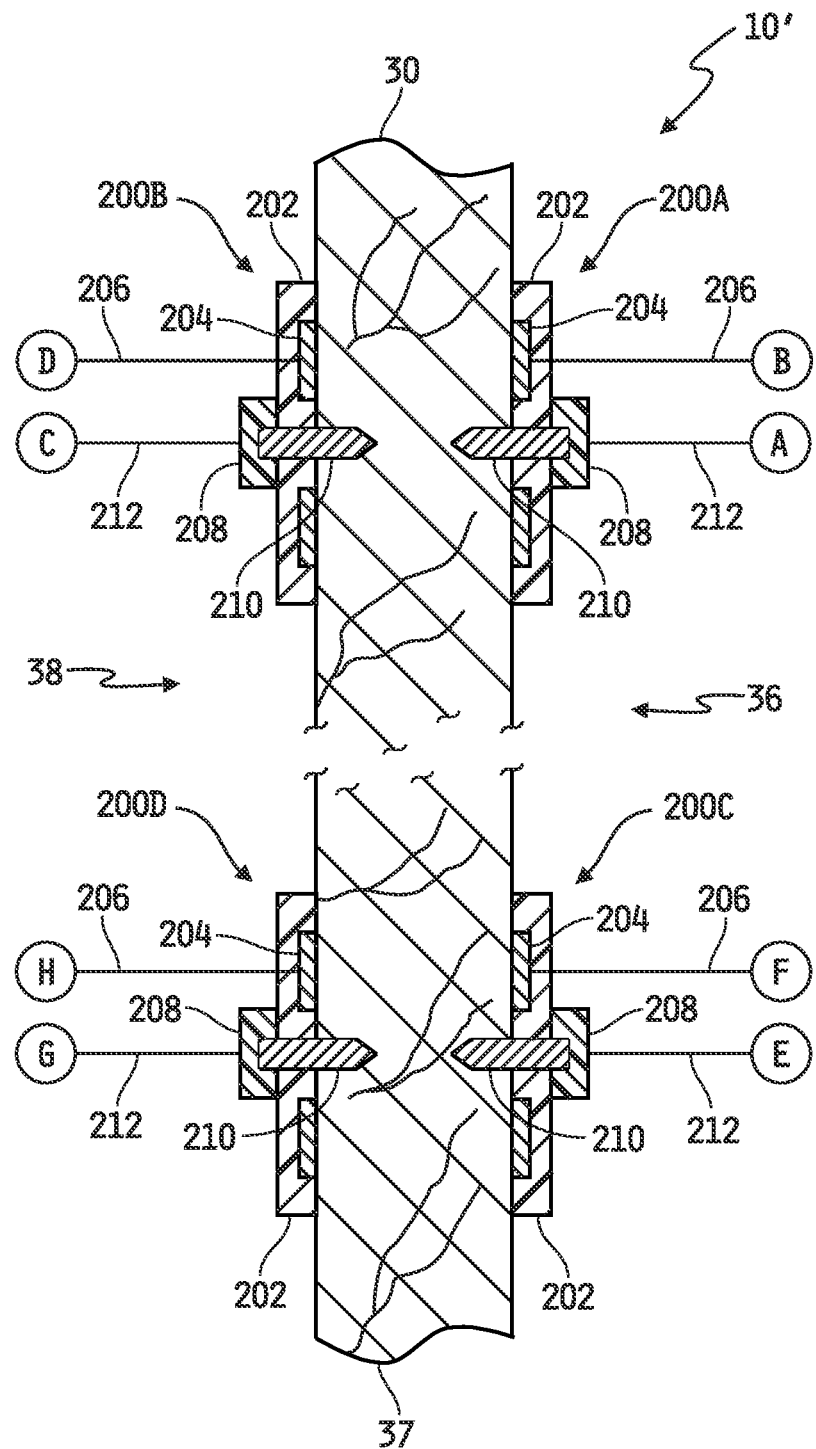
FIG. 11 is a cross-sectional view of the placed hybrid electrode assemblies illustrated in FIG. 10 as viewed along section lines 11-11.

Referring to FIGS. 10 and 11, for example, an implementation of an alternate auricular nerve field stimulation device 10' is shown in which the electrodes are provided in the form of two trans-auricular pairs 200A, 200B and 200C, 200D of the hybrid electrode assemblies 200. The hybrid electrode assembly 200A may illustratively be placed on the ventral aspect 36 of the auricle 30 generally above the antihelix 33 and in the triangular fossa 35, and the hybrid electrode assembly 200B may be placed on the dorsal aspect 38 across from the hybrid electrode assembly 200A such that the electrode assemblies 200A, 200B form a trans-auricular pair of electrodes. The hybrid electrode assembly 200C may, in the illustrated embodiment, be placed on the ventral aspect 36 of the ear lobe 37, and the hybrid electrode assembly 200D may be placed on the dorsal aspect 38 of the ear lobe 37 across from the hybrid electrode assembly 200C such that the electrode assemblies 200C, 200D form another trans-auricular pair of electrodes. It will be understood that in other implementations either or both trans-auricular pairs of the electrode assemblies 200A-200D may be placed at other locations along the auricle, and/or that the device 10' may include two or more additional trans-auricular pairs of hybrid electrode assemblies 200 and/or non-percutaneous electrodes placed at any location(s) along the auricle 30.

In any case, the hybrid electrode assemblies 200 may, in some embodiments, be carried by, i.e., be operatively coupled to, the flexible carrier 12 illustrated in FIGS. 1-4 and 7, although in other embodiments the hybrid electrode assemblies may each be individually coupled to the auricle 30. In the latter case, each of the housings 202 may illustratively be fitted with an individual, adhesive-backed, flexible carrier as described above. Alternatively, a suitable adhesive or other attachment medium may be applied to the region 216 of the housing 202 for promoting and maintaining contact between the ring 204 and the skin surface of the auricle 30. A removable film, such as the film 22 described above, may be used to protect such adhesive or other attachment medium prior to placement of the electrode assemblies 200.

The electrical conductors 208, 212 of the hybrid electrode assemblies 200A-200D are electrically coupled to the electrical circuitry 14 similarly as illustrated in FIG. 1, although electrical control of the device 10' differs from that of the devices 10, 100 in that the electrical circuitry 14 in the device 10' has independent control of each of two electrode structures within each electrode assembly 200A-200D. Example processes for controlling the hybrid electrode assemblies 200A-200D will be described in detail below. The electrical circuitry 14 may, as illustrated in FIG. 3, be attachable to the patient, e.g., behind the ear 32 or other location. In alternate embodiments, the electrical circuitry 14 may be housed in a suitable circuitry housing that may be carried by and/or be attached to the patient.

In the example illustrated in FIGS. 10 and 11, each hybrid electrode assembly 200A-200D is connected to two insulated electrical conductors 208, 212, as illustrated in FIGS. 9A and 9B and described above, for a total of eight electrical conductors. In FIG. 11, the electrical conductors 212 electrically coupled to the needle electrodes 210 are labeled A, C, E and G, and the electrical conductors 208 electrically coupled to the ring electrodes 204 are labeled B, D, F and H respectively. The electrical circuit 14 may be programmed or otherwise configured to selectively apply electrical stimulation signals, e.g., in the form of voltage or voltage differentials, to various combinations of the electrodes A-H, simultaneously, individually and/or sequentially and with any desired signal attributes as described above, for the purpose of causing corresponding currents to flow through the auricle 30 to provide therapy by stimulating at least one auricular nerve field within the auricle 30.

In one embodiment, the electrical circuitry 14 is illustratively configured to selectively supply voltages/currents solely to the percutaneously inserted needle electrodes 210 during a first phase of electrical stimulation treatment followed by selectively supplying voltages/currents solely to the non-percutaneous ring electrodes 204 during a second phase of electrical stimulation treatment separate from the first phase. In some such embodiments, any number of first phase treatments may be carried out prior to conducting each second phase treatment and vice versa. In one particular example implementation, each first phase treatment is following by one second phase treatment. In another example implementation, two first phase treatments are conducted, followed by one second phase treatment, followed by two first phase treatments, and so forth. In yet another example implementation, three or four first phase treatments are conducted, followed by one second phase treatment, followed by three or four first phase treatments, and so forth. In any of the foregoing examples, alternate implementations may include conducting two or more second phase treatments between each one or more first phase treatments. In still other alternate embodiments, multiple second phase treatments may conducted between each single first phase treatment. Those skilled in the art will recognize other treatment combinations, and it will be understood that all such other combinations are intended to fall within the scope of this disclosure.

An example therapy sequence of electrical stimulation signals applied by the circuitry 14 to the electrodes A-H during successive first and second phase treatment sequences are the following, although those skilled in the art will recognize that these treatment sequences represent only one of many different possible sequence combinations and therapy approaches that may be implemented using the device 10'. It will be understood that all such different sequence combinations and/or therapy approaches implementable using the device 10' are intended to fall within the scope of this disclosure.

Example Therapy Sequence
First Phase Treatment:

The following example first phase treatment sequence utilizes only the needle electrodes A, C, E and G, with an arbitrary one of the needle electrodes A, C, E and G used as a ground or reference electrode. In this example, needle electrode G will be used as the reference electrode, although it will be understood that the reference electrode in other therapy sequences and/or in other instances of the first phase treatment in this example therapy sequence may be any of the other needle electrodes A, C and E. The following pattern of items 1-8 is illustratively repeated sequentially for P time units with a rest or pause time of Q time units following repeated execution of the pattern of items 1-8 for P time units.

1. Apply S volts simultaneously to A, C and E at T hertz for U time units.
2. Rest or pause V time units.
3. Apply S volts simultaneously to A, C and E at W hertz for U time units.
4. Rest or pause V time units.
5. Apply −S volts simultaneously to A, C and E at T hertz for U time units.
6. Rest or pause V time units.
7 Apply −S volts simultaneously to A, C and E at W hertz for U time units.
8. Rest or pause V time units.

Example values of variables P-W are the following, although it will be understood that in other implementations one or more of P-W may take on different values:

P=15 minutes.
Q=2 minutes.
S=3.2 volts.
T=1 Hz.
U=1 millisecond.
V=2 seconds.
W=10 Hz.

It will be further understood that in some embodiments one or more of the items 1-8 may be omitted and/or executed at a different point in the pattern, such that the sequential pattern may include any combination of any of items 1-8 executed in any order.

Second Phase Treatment:

The following second phase treatment sequence utilizes only the ring electrodes B, D, F and H, which will assume the use of two ground reference-decoupled gating circuits controllable to selectively apply voltages and voltage differentials to the electrodes B, D, F and H as illustrated in FIG. 6 with respect to electrodes A, B, C and D thereof. In this regard, gating combination 1 refers to a positive voltage applied by VG1 between electrodes B and D, and a separate (i.e., decoupled) positive voltage simultaneously applied by VG2 between electrodes E and F, gating combination 2 refers to gating combination 1 with the polarities of VG1 and VG2 reversed, gating combination 3 refers to a positive voltage applied by VG1 between electrodes B and H, and a separate (i.e., decoupled) positive voltage simultaneously applied by VG2 between electrodes F and D, and gating combination 4 refers to gating combination 3 with the polarities of VG1 and VG2 reversed.

The following pattern of items 1-16 is illustratively repeated sequentially for P time units with a rest or pause time between each repeated pattern (in which no electrical stimulation signals are applied) of Q time units.

1. Apply S volts according to combination 1 at T hertz for U time units.
2. Rest or pause V time units.
3. Apply S volts according to combination 2 at T hertz for U time units.
4. Rest or pause V time units.
5. Apply S volts according to combination 1 at W hertz for U time units.
6. Rest or pause V time units.
7 Apply S volts according to combination 2 at W hertz for U time units.
8. Rest or pause V time units.
9. Apply S volts according to combination 3 at T hertz for U time units.
10. Rest or pause V time units.
11. Apply S volts according to combination 4 at T hertz for U time units.
12. Rest or pause V time units.
13. Apply S volts according to combination 3 at W hertz for U time units.
14. Rest or pause V time units.
15. Apply S volts according to combination 4 at W hertz for U time units.
16. Rest or pause V time units.

Example values of variables P-W are the following, although it will be understood that in other implementations one or more of P-W may take on different values:
P=15 minutes.
Q=1 minute.
S=4.2 volts.
T=1 Hz.
U=1 millisecond.
V=2 seconds.
W=10 Hz.

It will be further understood that in some embodiments one or more of the items 1-16 may be omitted and/or executed at a different point in the pattern, such that the sequential pattern may include any combination of any of items 1-16 executed in any order. In any case, a sequence of one or more cycles of the first phase treatment followed by one or more cycles of the second phase treatment is illustratively carried out over a time period of 120 hours, after which the therapy is discontinued. In one non-limiting example implementation, at least 2 sequences of the first phase treatment are carried out between each second phase treatment. In some alternate embodiments, the voltage applied between electrodes B and H in any or all of steps 9, 11, 13 and 15 may have a different frequency than the voltage applied between electrodes F and D so as to establish an interferential current in a space within the auricle 30 intersected by the two currents flowing between the pairs B, H and F, D of the four electrodes B, H, F and D.

Fourth Embodiment

Figure 12:
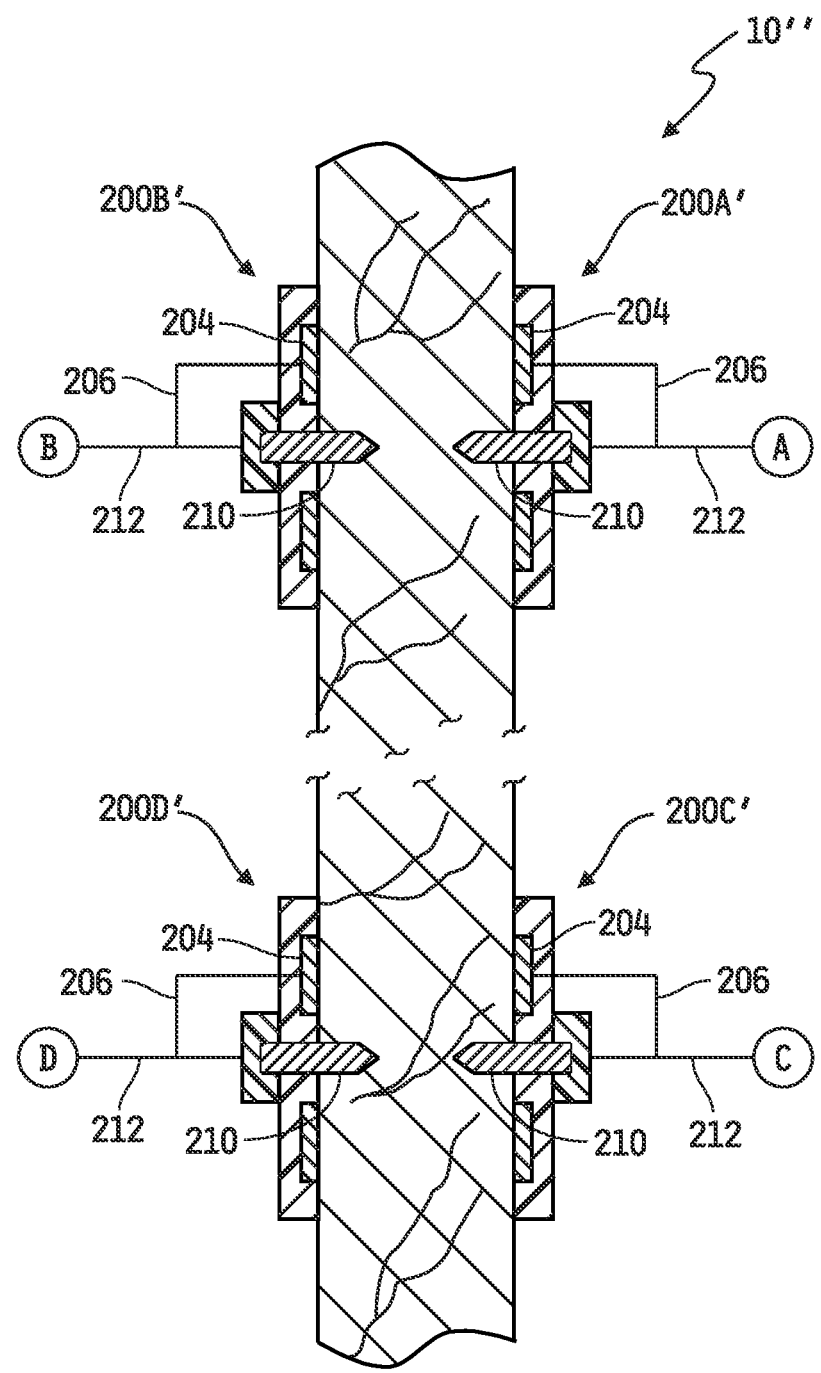
FIG. 12 is a cross-sectional view similar to FIG. 11 illustrating an alternate wire connection scheme to the hybrid electrode assemblies of FIG. 11.

The third embodiment of the auricular nerve field stimulation device 10' is illustrated in FIGS. 9A-11 and described above as including eight electrodes A-H each with a separate, dedicated electrical conductor connected to the electrical circuitry 14 such that the electrical circuitry 14 has independent control of each electrode A-H. In a fourth embodiment 10", in contrast, the ring electrode 204 of each electrode assembly 200A'-200D' is electrically connected to the needle electrode 210 thereof, as illustrated by example in FIG. 12. Such connections may illustratively be made within the housing(s) 202, 208 or outside of the housing(s) 202, 208 adjacent thereto, and in either case only a single electrical conductor extends between the electrical circuitry 14 and each of the electrode assemblies 200A'-200D'. In the embodiment illustrated in FIG. 12, electrical signals applied to the electrode assemblies 200A'-200D' are simultaneously applied to each electrode 204, 210 thereof. In this regard, conducting the first phase treatment described above not only provides percutaneous therapy via the needle electrodes 210 as described above, but further simultaneously provides conventional TENS therapy via the ring electrodes 204. Similarly, conducting the second phase treatment described above not only provides second phase treatment therapy via the ring electrodes 204 as described above, but further simultaneously provides focused second phase treatment therapy via the percutaneously inserted needle electrodes 210. It will be understood that further alternate embodiments are contemplated in which the ring electrode(s) 204 is/are electrically connected to the needle electrode(s) 210 in fewer than all of the electrode assemblies 200A'-200D', e.g., only in one or more of the electrode assemblies 200A'-200D'.

While the disclosure has been illustrated and described in detail in the drawings and foregoing description, such an illustration and description is to be considered as exemplary and not restrictive in character, it being understood that only illustrative embodiments have been shown and described and that all changes and modifications consistent with the disclosure and recited claims are desired to be protected.

What is claimed is:

1. A non-percutaneous trans-auricular nerve field stimulation device, comprising:
a first plurality of spaced-apart electrically conductive electrodes each arranged to non-percutaneously contact a ventral aspect of an auricle of a human ear,
a second plurality of spaced-apart electrically conductive electrodes each arranged to non-percutaneously contact a dorsal aspect of the auricle, and
electrical circuitry coupled to the first and second plurality of electrodes and configured to selectively apply electrical stimulation signals to at least one of the first plurality of electrodes and the second plurality of electrodes to cause a first set of trans-auricular currents to flow through the auricle between the first plurality of electrodes and respective ones of the second plurality of electrodes paired therewith according to a first pairing, and to cause a second set of trans-auricular currents to flow through the auricle between the first plurality of electrodes and respective ones of the second plurality of electrodes paired therewith according to a second pairing different from the first pairing, the first and second sets of trans-auricular currents to stimulate at least one auricular nerve field within the auricle,
wherein each of the first plurality of electrodes is offset relative to a respective one of the second plurality of electrodes according to the second pairing such that the second set of trans-auricular currents flow diagonally through the auricle between the offset pairs of the first and second plurality of electrodes.

2. The device of claim 1, wherein each of the first plurality of electrodes is aligned with a respective one of the second plurality of electrodes according to the first pairing such that the first set of trans-auricular currents flow between the aligned ones of the first and second plurality of electrodes in a direction parallel to a transverse plane of the auricle.

3. The device of claim 1, further comprising a flexible carrier to which the first plurality of electrodes, the second plurality of electrodes and the electrical circuitry are all mounted, and means for attaching the flexible carrier to at least a portion of the auricle, wherein the flexible carrier includes:
an elongated main body sized and configured to extend longitudinally along at least a portion a helix of the auricle and to wrap transversely at least partially about the at least the portion of the helix,
an upper wing member at one end of the elongated main body and sized to extend over at least a first portion of the ventral aspect of the auricle and to extend over at least a first portion of the dorsal aspect of the auricle, at least one of the plurality of first electrodes and at least one of the plurality of second electrodes mounted to the upper wing member,
a lower wing member at an opposite end of the elongated main body and sized to extend over at least a second portion of the ventral aspect of the auricle spaced apart from the at least a first portion of the ventral aspect and to extend over at least a second portion of the dorsal aspect of the auricle spaced apart from the at least a first portion of the dorsal aspect, at least another of the plurality of first electrodes and at least another of the plurality of second electrodes mounted to the lower wing member,
an electrical circuit mounting portion extending from the elongated main body, the electrical circuitry mounted to the electrical circuit mounting portion, and
electrical conductors connected between the electrical circuitry and each of the first and second plurality of electrodes.

4. The device of claim 3, wherein the upper wing member comprises:
a first wing extending transversely away from the one end of the elongated main body in a first direction and sized to extend over the at least the first portion of the ventral aspect of the auricle, the at least one of the first plurality of electrodes mounted to the first wing of the upper wing member and configured to non-percutaneously contact the at least the first portion of the ventral aspect, and
a second wing extending transversely away from the one end of the elongated main body in a second direction opposite the first direction and sized to extend over the at least the first portion of the dorsal aspect of the auricle, the at least one of the second plurality of electrodes mounted to the second wing of the upper wing member and configured to non-percutaneously contact the at least the second portion of the dorsal aspect
and wherein the lower wing member comprises:
a first wing extending transversely away from the opposite end of the elongated main body in a first direction and sized to extend over the at least the second portion of the ventral aspect of the auricle, the at least another of the first plurality of electrodes mounted to the first wing of the lower wing member and configured to non-percutaneously contact the at least the second portion of the ventral aspect, and
a second wing extending transversely away from the opposite end of the elongated main body in a second direction opposite the first direction and sized to extend over at the second portion of the dorsal aspect of the auricle, the at least another of the second plurality of electrodes mounted to the second wing of the lower wing member and configured to non-percutaneously contact the at least the second portion of the dorsal aspect.

5. The device of claim 1, wherein the electrical circuitry comprises:
one or more electrical power sources,
at least one control circuit coupled to at least one of the one or more electrical power sources and programmed to generate electrical stimulation control signals, and
two or more gating circuits coupled to at least one of the one or more electrical power sources and to the at least one control circuit, the two or more gating circuits responsive to the generated electrical stimulation control signals to produce the electrical stimulation signals using electrical power produced by the at least one of the one or more electrical power sources.

6. The device of claim 5, wherein the two or more gating circuits share a common electrical power reference potential.

7. The device of claim 5, wherein each of the two or more gating circuits includes an electrical power reference, and wherein the electrical power references of the two or more gating circuits are decoupled from one another.

8. The device of claim 5, wherein the at least one control circuit is programmed to control at least one of a polarity of one or more of the electrical stimulation control signals, a frequency of one or more of the electrical stimulation control signals, a duty cycle of one or more of the electrical stimulation control signals, a duration of one or more of the electrical stimulation control signals, a pause time between adjacent applications of one or more of the electrical stimulation control signals and an overall therapy duration in which at least one of the electrical stimulation control signals is produced.

9. A non-percutaneous trans-auricular nerve field stimulation device, comprising:
a first electrically conductive electrode arranged to non-percutaneously contact a first portion of a ventral aspect of an auricle of a human ear,
a second electrically conductive electrode arranged to non-percutaneously contact a first portion of a dorsal aspect of the auricle opposite the first portion of the ventral aspect,
a third electrically conductive electrode arranged to non-percutaneously contact a second portion of the ventral aspect of auricle spaced apart from the first portion of the ventral aspect,
a fourth electrically conductive electrode arranged to non-percutaneously contact a second portion of the dorsal aspect of the auricle opposite the second portion of the ventral aspect, and
electrical circuitry coupled to the first, second third and fourth electrodes, the electrical circuitry configured to (i) selectively apply a first electrical stimulation signal to at least one of the first and second electrodes to cause a first trans-auricular current to flow therebetween and transversely through the auricle in a direction parallel to a transverse plane of the auricle, (ii) selectively apply a second electrical stimulation signal to at least one of the third and fourth electrodes to cause a second trans-auricular current to flow therebetween and transversely through the auricle in the direction parallel to the transverse plane of the auricle, (iii) selectively apply a third electrical stimulation signal to at least one of the second and third electrodes to cause a third trans-auricular current to flow therebetween and diagonally through the auricle, and (iv) selectively apply a fourth electrical stimulation signal to at least one of the first and fourth electrode to cause a fourth trans-auricular current to flow therebetween and diagonally through the auricle.

10. The device of claim 9, further comprising a flexible carrier to which the first plurality of electrodes, the second plurality of electrodes and the electrical circuitry are all mounted, and means for attaching the flexible carrier to at least a portion of the auricle, wherein the flexible carrier includes:
an elongated main body sized and configured to extend longitudinally along at least a portion a helix of the auricle and to wrap transversely at least partially about the at least the portion of the helix,
an upper wing member at one end of the elongated main body and sized to extend over at least the first portion of the ventral aspect of the auricle and over at least the first portion of the dorsal aspect of the auricle, the first and second electrodes mounted to the upper wing member,
a lower wing member at an opposite end of the elongated main body and sized to extend over at least the second portion of the ventral aspect of the auricle spaced apart from the a first portion of the ventral aspect and over at least the second portion of the dorsal aspect of the auricle spaced apart from the first portion of the dorsal aspect, the third and fourth electrodes mounted to the lower wing member,
an electrical circuit mounting portion extending from the elongated main body, the electrical circuitry mounted to the electrical circuit mounting portion, and
electrical conductors connected between the electrical circuitry and each of the first, second, third and fourth electrodes.

11. The device of claim 9, wherein the electrical circuitry is programmed to sequentially and repeatedly execute the following steps (a) through (h) for a predefined pattern duration:
(a) execute (i) and (ii) simultaneously at a first frequency, with a first duty cycle and for a first application duration to simultaneously cause the first trans-auricular current to flow from the first electrode toward the second electrode and to cause the second trans-auricular current to flow from the third electrode toward the fourth electrode,
(b) pause after (a) for a first pause duration,
(c) after (b), execute (i) and (ii) simultaneously at a second frequency, higher than the first frequency, with the first duty cycle and for the first application duration to simultaneously cause the first trans-auricular current to flow from the first electrode toward the second electrode and to cause the second trans-auricular current to flow from the third electrode toward the fourth electrode,
(d) pause after (c) for the first pause duration,
(e) execute (iii) and (iv) simultaneously at the first frequency, with the first duty cycle and for the first application duration to simultaneously cause the third trans-auricular current to flow from the third electrode toward the second electrode and to cause the fourth trans-auricular current to flow from the first electrode toward the fourth electrode,
(f) pause after (e) for the first pause duration,
(g) execute (iii) and (iv) simultaneously at the second frequency, with the first duty cycle and for the first application duration to simultaneously cause the third trans-auricular current to flow from the third electrode toward the second electrode and to cause the fourth trans-auricular current to flow from the first electrode toward the fourth electrode, and
(h) pause after (g) for the first pause duration.

12. The device of claim 11, wherein the electrical circuitry is programmed to (1) sequentially and repeatedly execute the pattern of (a) through (h) for the predefined pattern duration, (2) to thereafter pause for a second pause duration, and (3) to sequentially and repeatedly execute (1) and (2) for a predefined therapy duration.

13. The device of claim 11, wherein, following step (b) but prior to step (c), the electrical circuitry is programmed to (A) execute (i) and (ii) simultaneously at the first frequency, with the first duty cycle and for the first application duration to simultaneously cause the first trans-auricular current to flow from the second electrode toward the first electrode and to cause the second trans-auricular current to flow from the fourth electrode toward the third electrode, and (B) pause after (A) for the first pause duration.

14. The device of claim 11, wherein, following step (d) but prior to step (e), the electrical circuitry is programmed to (C) execute (i) and (ii) simultaneously at the second frequency, with the first duty cycle and for the first application duration to simultaneously cause the first trans-auricular current to flow from the second electrode toward the first electrode and to cause the second trans-auricular current to flow from the fourth electrode toward the third electrode, and (D) pause after (C) for the first pause duration.

15. The device of claim 11, wherein, following step (f) but prior to step (g), the electrical circuitry is programmed to (E) execute (iii) and (iv) simultaneously at the first frequency, with the first duty cycle and for the first application duration to simultaneously cause the third trans-auricular current to flow from the second electrode toward the third electrode and to cause the fourth trans-auricular current to flow from the fourth electrode toward the first electrode, and (F) pause after (E) for the first pause duration.

16. The device of claim 11, wherein, following step (h) but prior to re-executing step (a), the electrical circuitry is programmed to (G) execute (iii) and (iv) simultaneously at the second frequency, with the first duty cycle and for the first application duration to simultaneously cause the third trans-auricular current to flow from the second electrode toward the third electrode and to cause the fourth trans-auricular current to flow from the fourth electrode toward the first electrode, and (H) pause after (G) for the first pause duration.

17. A non-percutaneous trans-auricular nerve field stimulation device, comprising:
a first electrically conductive electrode arranged to non-percutaneously contact a ventral aspect of an auricle of a human ear,
a second electrically conductive electrode arranged to non-percutaneously contact a dorsal aspect of the auricle opposite the first electrically conductive electrode,
a third electrically conductive electrode arranged to non-percutaneously contact the ventral aspect of auricle spaced apart from the first electrically conductive electrode, a fourth electrically conductive electrode arranged to non-percutaneously contact the dorsal aspect of the auricle opposite the third electrically conductive electrode, and electrical circuitry coupled to the first, second third and fourth electrodes, the electrical circuitry configured to (i) selectively apply a first electrical stimulation signal of a first frequency to at least one of the first and fourth electrode to cause a first trans-auricular current to flow therebetween and diagonally through the auricle, and (ii) selectively apply a second electrical stimulation signal of a second frequency, different than the first frequency, to at least one of the second and third electrodes to cause a second trans-auricular current to flow therebetween and diagonally through the auricle, wherein the first and second trans-auricular currents define an interferential current within the auricle.

18. The device of claim 17, wherein the electrical circuitry comprises:

one or more electrical power sources, at least one control circuit coupled to at least one of the one or more electrical power sources and programmed to generate electrical stimulation control signals, and one or more gating circuits coupled to at least one of the one or more electrical power sources and to the at least one control circuit, the one or more gating circuits responsive to the generated electrical stimulation control signals to produce the first and second electrical stimulation signals using electrical power produced by the at least one of the one or more electrical power sources.

19. The device of claim 18, wherein the at least one control circuit is programmed to control at least one of a polarity of one or more of the electrical stimulation control signals, a frequency of one or more of the electrical stimulation control signals, a duty cycle of one or more of the electrical stimulation control signals, a duration of one or more of the electrical stimulation control signals, a pause time between adjacent applications of one or more of the electrical stimulation control signals and an overall therapy duration in which at least one of the electrical stimulation control signals is produced.

* * * * *